(12) United States Patent
Fandl et al.

(10) Patent No.: US 10,598,669 B2
(45) Date of Patent: *Mar. 24, 2020

(54) ISOLATING CELLS EXPRESSING SECRETED PROTEINS

(71) Applicant: Regeneron Pharmaceuticals, Inc., Tarrytown, NY (US)

(72) Inventors: James P. Fandl, LaGrangeville, NY (US); Gang Chen, Yorktown Heights, NY (US); Neil Stahl, Carmel, NY (US); George D. Yancopoulos, Yorktown Heights, NY (US)

(73) Assignee: Regeneron Pharmaceuticals, Inc., Tarrytown, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 16/352,154

(22) Filed: Mar. 13, 2019

(65) Prior Publication Data

US 2019/0376981 A1 Dec. 12, 2019

Related U.S. Application Data

(60) Continuation of application No. 14/885,460, filed on Oct. 16, 2015, now Pat. No. 10,261,093, which is a continuation of application No. 14/565,767, filed on Dec. 10, 2014, now abandoned, which is a continuation of application No. 13/738,349, filed on Jan. 10, 2013, now Pat. No. 9,389,236, which is a continuation of application No. 12/240,541, filed on Sep. 29, 2008, now abandoned, which is a continuation-in-part of application No. 11/434,403, filed on May 15, 2006, now Pat. No. 7,435,553, which is a continuation of application No. 11/099,158, filed on Apr. 5, 2005, now abandoned, which is a division of application No. 10/050,279, filed on Jan. 16, 2002, now Pat. No. 6,919,183.

(60) Provisional application No. 60/261,999, filed on Jan. 16, 2001.

(51) Int. Cl.
| | |
|---|---|
| G01N 33/566 | (2006.01) |
| G01N 33/68 | (2006.01) |
| G01N 33/569 | (2006.01) |
| C12N 15/65 | (2006.01) |

(52) U.S. Cl.
CPC ......... *G01N 33/6854* (2013.01); *C12N 15/65* (2013.01); *G01N 33/566* (2013.01); *G01N 33/56966* (2013.01); *G01N 2333/7051* (2013.01)

(58) Field of Classification Search
None
See application file for complete search history.

(56) References Cited

U.S. PATENT DOCUMENTS

| | | |
|---|---|---|
| 5,635,354 A | 6/1997 | Kourilsky et al. |
| 5,916,771 A | 6/1999 | Hori et al. |
| 6,080,840 A | 6/2000 | Slanetz |
| 6,232,066 B1 | 5/2001 | Felder et al. |
| 6,287,784 B1 | 9/2001 | Godowski et al. |
| 6,482,655 B1 | 11/2002 | Wei et al. |
| 6,610,485 B1 | 8/2003 | Tsuchiya et al. |
| 6,623,957 B2 | 9/2003 | Ward |
| 6,919,183 B2 | 7/2005 | Fandl et al. |
| 6,927,044 B2 | 8/2005 | Stahl |
| 7,329,731 B2 | 2/2008 | Jakobsen |
| 7,430,476 B2 | 9/2008 | Carr et al. |
| 7,435,553 B2 | 10/2008 | Fandl et al. |
| 7,585,946 B2 | 9/2009 | Fandl et al. |
| 7,700,302 B2 | 4/2010 | Hua et al. |
| 7,879,984 B2 | 2/2011 | Martin et al. |
| 9,758,592 B2 | 9/2017 | Deshpande et al. |
| 2002/0039580 A1 | 4/2002 | Browning et al. |
| 2002/0168702 A1 | 11/2002 | Fandl et al. |
| 2003/0082814 A1 | 5/2003 | Ward |
| 2005/0186623 A1 | 8/2005 | Fandl et al. |
| 2006/0234311 A1 | 10/2006 | Fandl et al. |
| 2009/0137416 A1 | 5/2009 | Fandl et al. |
| 2010/0227774 A1 | 9/2010 | Hua et al. |

(Continued)

FOREIGN PATENT DOCUMENTS

| | | |
|---|---|---|
| DE | 19900635 | 7/2000 |
| EP | 0107509 | 5/1984 |

(Continued)

OTHER PUBLICATIONS

Amersham Biosciences. 2001. Protein A. Whole document. Retrieved from https://www.gelifesciences.com/gehcls_images/GELS/Related%20Content/Files/1314723116657/litdoc18106056_20161013130948.pdf.

Barnes, et al. 2000. Advances in animal cell recombinant protein production: GS-NSO expression system. Cytotechnology 32: 109-123.

Bebbington, et al. 1992. High-level expression of a recombinant antibody from myeloma cells using a glutamine synthetase gene as an amplifiable selectable marker. Bio/Technology 10: 169-175.

(Continued)

*Primary Examiner* — Zachary S Skelding
(74) *Attorney, Agent, or Firm* — Honingman LLC; Kelly T. Murphy; Jonathan P. O'Brien

(57) ABSTRACT

A method of detecting and isolating cells that produce a secreted protein of interest (POI), for example, an antibody, comprising: a) providing a eukaryotic cell comprising (i) a nucleic acid encoding the POI, and (ii) a nucleic acid encoding a cell surface capture molecule, which comprises a membrane anchor and is capable of binding the POI; (b) culturing the cell under conditions in which the POI and cell surface capture molecule are expressed, and a POI-cell surface capture molecule complex is formed intracellularly and displayed on the cell surface; c) detecting the surface-displayed POI by contacting the cells with a detection molecule, which binds the POI; and d) isolating cells based on the detection molecule.

20 Claims, 23 Drawing Sheets

Specification includes a Sequence Listing.

(56) References Cited

U.S. PATENT DOCUMENTS

| | | |
|---|---|---|
| 2010/0331527 A1 | 12/2010 | Davis et al. |
| 2011/0009280 A1 | 1/2011 | Hufton et al. |
| 2012/0322672 A1 | 12/2012 | Hua et al. |
| 2014/0017695 A1 | 1/2014 | Fandl et al. |
| 2014/0072979 A1 | 3/2014 | Fandl et al. |
| 2014/0072980 A1 | 3/2014 | Fandl et al. |
| 2014/0134719 A1 | 5/2014 | Deshpande et al. |
| 2015/0160215 A1 | 6/2015 | Fandl et al. |
| 2016/0033530 A1 | 2/2016 | Fandl et al. |
| 2017/0241887 A1 | 8/2017 | Fandl et al. |

FOREIGN PATENT DOCUMENTS

| | | |
|---|---|---|
| EP | 1392859 | 5/2006 |
| EP | 2522724 | 11/2012 |
| EP | 2949667 | 12/2015 |
| WO | WO94009117 | 4/1994 |
| WO | WO97029131 | 8/1997 |
| WO | WO99058977 | 11/1999 |
| WO | WO02057423 | 7/2002 |
| WO | WO10151792 | 12/2010 |
| WO | WO13166236 | 11/2013 |
| WO | WO14078475 | 5/2014 |

OTHER PUBLICATIONS

Berglund, et al., 2008. The epitope space of the human proteome. Protein Science, 17(4), pp. 606-613.

Boder, et al., 2000. "Directed evolution of antibody fragments with monovalent femtomolar antigen-binding affinity", PNAS, vol. 97, No. 20, pp. 10701-10705.

Boder, et al., 1997. "Yeast surface display for screening combinatorial polypeptide libraries", Nature Biotechnology, vol. 15, pp. 553-557.

Bonagura, et al., 1998. Mapping IgG epitopes bound by rheumatoid factors from immunized controls identifies disease-specific rheumatoid factors produced by patients with rheumatoid arthritis. The Journal of Immunology, 160(5), pp. 2496-2505.

Boria, I. et al. 2008. Primer sets for cloning the human repertoire of T cell receptor variable regions. BMC Immun. 9:50.

Carrol, S, and M. Al-Rubeai., 2004. "The selection of high-producing cell lines using flow cytometry and cell sorting." Expert opinion on biological therapy 4, No. 11: 1821-1829.

Crowe, et al. 1992. Humanized monoclonal antibody CAMPATH-1H: myeloma cell expression of genomic constructs, nucleotide sequence of cDNA constructs and comparison of effector mechanisms of myeloma and Chinese hamster ovary cell-derived material. Clin. Exp. Immunol. 87: 105-110.

Dangl and Herzenberg 1982. Selection of hybridomas and hybridoma variants using the fluorescence activated cell sorter. J. Immunol. Methods 52(1):1-14.

De Angelis. 1999. Why FRET over genomics? Physiol Genomics. 1(2): 93-99.

Dean, et al. 2000. Preparation of rodent monoclonal antibodies by in vitro somatic hybridization. Monoclonal Antibodies (Shepherd and Dean, Eds). Oxford University Press. 1-23.

Fernandes, S. et al. 2005. Simplified fluorescent multiplex PCR method for evaluation of the T-cell receptor Vbeta-chain repertoire. Clin. Diagn. Lab. Immunol. 12(4):477-483.

Genevee, C. et al. 1992. An experimentally validated panel of subfamily-specific oligonucleotide primers (V alpha 1-w29N beta 1-w24) for the study of human T cell receptor variable V gene segment usage by polymerase chain reaction. Eur. J. Immunol. 22:1261-1269.

Goeddel, D.V. 1990. Systems for heterologous gene expression. Meth. Enzymol. 185:3-7.

Gomi, et al.1990. The gene sequence and some properties of protein H. A novel IgG-binding protein. J Immunol. 144 (10): 4046-4052.

Gorski, J. et al. 1994. Circulating T cell repertoire complexity in normal individuals and bone marrow recipients analyzed by CDR3 size spectratyping. Correlation with immune status. J. Immunol. 152(10):5109-5119.

Moldenhauer, G., 2011. Bispecific antibodies from hybrid hybridoma. In Bispecific Antibodies, 29-46. Springer Berlin Heidelberg.

Gray, et al. 1995. Secretion capture and report web: use of affinity derivatized agarose microdroplets for the selection of hybridoma cells. J. Immunol. Methods 182(2):155-163.

Hamilton, R. and S.L. Morrison, 1993. Epitope mapping of human immunoglobulin-specific murine monoclonal antibodies with domain-switched, deleted and point-mutated chimeric antibodies. Journal of immunological methods, 158(1), pp. 107-122.

Hinz, T. and D. Kabelitz. 2000. Identification of the T-cell receptor alpha variable (TRAV) gene(s) in T-cell malignancies. J. Immnol. Methods. 246:145-148.

Hodges, E. et al. 2003. Diagnostic role of tests for T cell receptor (TCR) genes. J Clin Pathol 56:1-11.

Hybridoma Reagent Laboratory. 2012. Products Overview. Whole document. Retrieved from http://web.archive.org/web/20121028123111/http://www.hybridoma-reagent-laboratory.com/Company/CompanyProduct1.htm.

Johnston, S.L. et al. 1995. A novel method for sequencing members of multi-gene families. Nuc. Acids Res. 23 (15):3074-3075.

Klimka, et al., 2000. Human anti-CD30 recombinant antibodies by guided phage antibody selection using cell panning. British journal of cancer, 83(2), p. 252.

Kontermann, R., 2012. Dual targeting strategies with bispecific antibodies. In MAbs 4 (2), p. 182-197. Taylor & Francis.

Laugel, B. et al. 2005. Design of soluble recombinant T cell receptors for antigen targeting and T cell inhibition. J. Bio. Chem. 280(3): 1882-1892.

Lee, et al. 2003. Microbial cell-surface display. Trends Biotechnol. 21 (1 ):45-52.

Lefranc, et al., 2003. IMGT unique numbering for immunoglobulin and T cell receptor variable domains and Ig superfamily V-like domains. Devel. Comp. Immunol. 27:57-77.

Lefranc, et al., 2005. IMGT unique numbering for immunoglobulin and T cell receptor constant domains and Ig superfamily C-like domains. Devel. Comp. Immunol. 29: 185-203.

Li, Y. et al., 2005.Directed evolution of human T-cell receptors with picomolar affinities by phage display. Nat. Biotech. 23(3):349-354.

Manz, R., et al. 1995. Analysis and sorting of live cells according to secreted molecules, relocated to a cell-surface affinity matrix. PNAS USA 92(6):1921-1925.

Martel et al., 1988. Characterization of higher avidity monoclonal antibodies produced by murine B-cell hybridoma variants selected for increased antigen binding of membrane Ig. J. Immunol. 141(5):1624-1629.

Maynard, J, and G. Georgiou, 2000. Antibody engineering. Annual review of biomedical engineering. 2(1):339-76.

McKinney, et al. 1995. Optimizing antibody production in batch hybridoma cell culture. Journal of Biotechnology. 40: 31-48.

Mendelsohn, et al. 1999. Protein Interaction Methods—Toward an Endgame. Science. 284: 1948-1950.

Meng, et al., 2000. Green fluorescent protein as a second selectable marker for selection of high producing clones from transfected CHO cells. Gene 242(1-2):201-207.

Morrison, et al. 1988. Production and Characterization of Genetically Engineered Antibody Molecules. Clin. Chem. 34(9): 1668-1675.

Moysey, R. et al. 2004. Amplification and one-step expression cloning of human T cell receptor genes. Analy. Biochem. 326:284-286.

Nairn, Fluorescent Protein Tracing, Churchill Livingston, 1976, pp. 149-150.

Olsson, et al. 1987. Structure and evolution of the repetitive gene encoding *streptococcal* protein G. Eur. J. Biochem 168: 319-324.

Opekarova, et al. 2003. Specific lipid requirements of membrane proteins—a putative bottleneck in heterologous expression. Biochem. Biophys. Acta. 1610(1):11-22.

Pallavacini, et al., 1989. Rapid screening and selection of monoclonal antibodies by bivariate flow cytometric analyses. J. Immunol. Methods 117(1):99-106.

Pannetier, C. et al. 1995. T-cell repertoire diversity and clonal expansions in normal and clinical samples. Immunology Today 16(4):176-181.

(56) References Cited

OTHER PUBLICATIONS

Parks, et al. 1979. Antigen-specific identification and cloning of hybridomas with a fluorescence-activated cell sorter. PNAS 76(4):1962-1966.

Richman, Sa and D.M. Kranz. 2007. Display, engineering, and applications of antigen-specific T cell receptors. Biomol. Eng. 24:361-373.

Selvin. 2000. The renaissance of fluorescence resonance energy transfer. Nature Structural Biology. 7(9): 730-734.

Sondermann, et al. 2000. The 3.2—A crystal structure of the human IgG1 Fc fragment—FcγRIII complex. Nature. 406 (6793): 267-273.

Stenroos, et al. 1998. Homogeneous time-resolved IL-21L-2Rx Assay using Fluorescence Resonance Energy Transfer. Cytokine. 10(7): 495-499.

USPTO English Translation of DE 199 00 635.

Van Dongen, JJM. et al. 2003. Design and standardization of PCR primers and protocols for detection of clonal immunoglobulin and T-cell receptor gene recombinations in suspect lymphoproliferations: Report of the BIOMED-2 Concerted Action BMH4-CT98-3936. Leukemia 17:2257-2317.

Van Vugt, et al. 1999. The FcγRla (CD64) Ligand Binding Chain Triggers Major Histocompatibility Complex Class II Antigen Presentation Independently of Its Associated FcR γ-Chain. Blood. 94(2): 808-817.

Witzenbichler, et al. 1998. Chemotactic Properties of Angiopoietin-1 and -2, Ligands for the Endothelial-specific Receptor Tyrosine Kinase Tie2. The Journal of Biological Chemistry. 273(29): 18514-18521.

Wlodarski, M.W. et al. 2005. Pathologic clonal cytotoxic T-cell responses: nonrandom nature of the T-cell receptor restriction in large granular lymphocyte leukemia. Blood 106(8):2769-2780.

Wlodarski, M.W. et al. 2006. Molecular strategies for detection and quantitation of clonal cytotoxic T-cell responses in aplastic anemia and myelodysplastic syndrome. Blood 108(8):2632-2641.

Vidarsson G. et al. 2014. IgG subclasses and allotypes: from structure to effector functions. Front. Immunol. 5:520.

| 4SC622 | IgG Species | Cells Labeled (%) |
|---|---|---|
| − | − | 0.7 |
| + | − | 93.2 |
| + | human | 0.8 |
| + | rat | 2.0 |
| + | rabbit | (1.0) |
| + | canine | 4.8 |
| + | bovine | 92.0 |
| + | ovine | 91.7 |

FIG.3

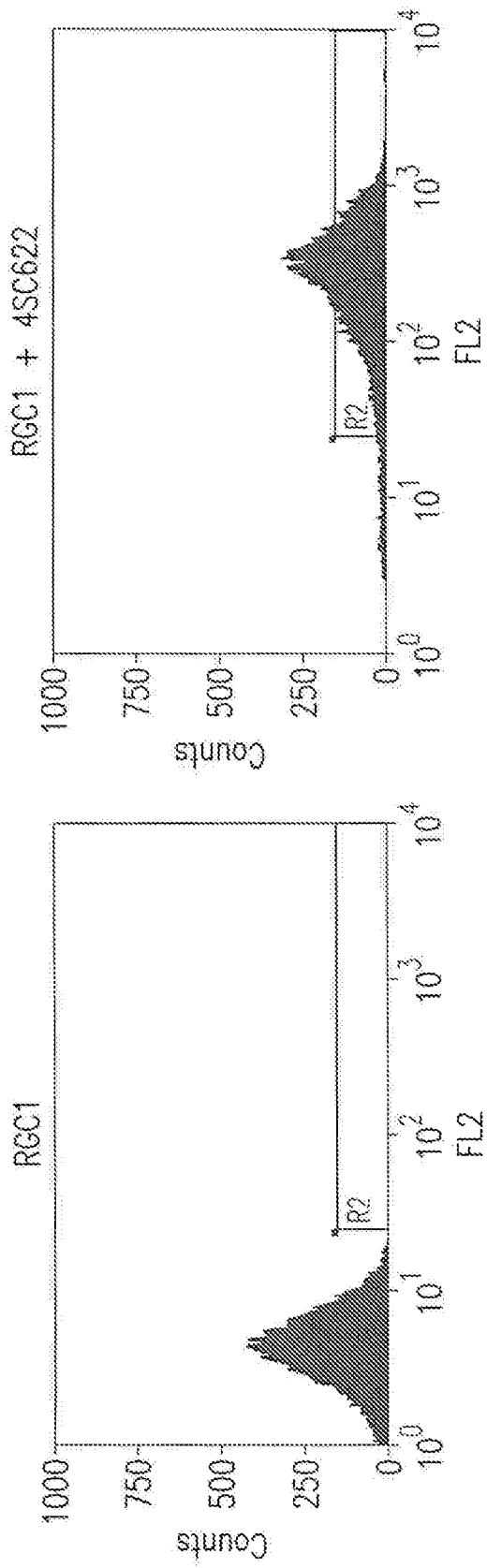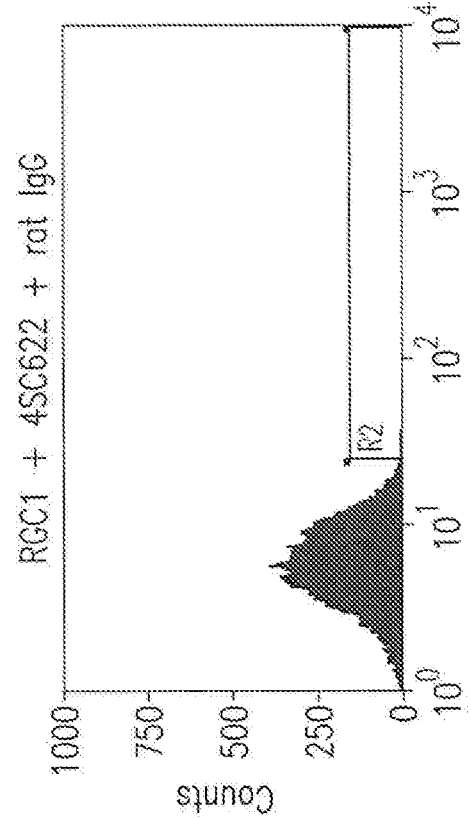
FIG. 4A
FIG. 4B
FIG. 4C

| Protein | Transient | Hand-picked CHO K1 Stable Cell Lines | | RGC1-derived Stable Cell Lines | |
|---|---|---|---|---|---|
| | µg/ml | Sp.Prod. (pg/cell/day) | # clones screened | Sp.Prod. (pg/cell/day) | # clones screened |
| 4SC622 | 1.1 | 12 | 2700 | 12 | 6 |
| h VEGF-R1R2 | 33 | 68 | 190 | 77 | 62 |
| h VEGF-R1R3 | 27 | 5 | 100 | 22.6 | 42 |

FIG.7

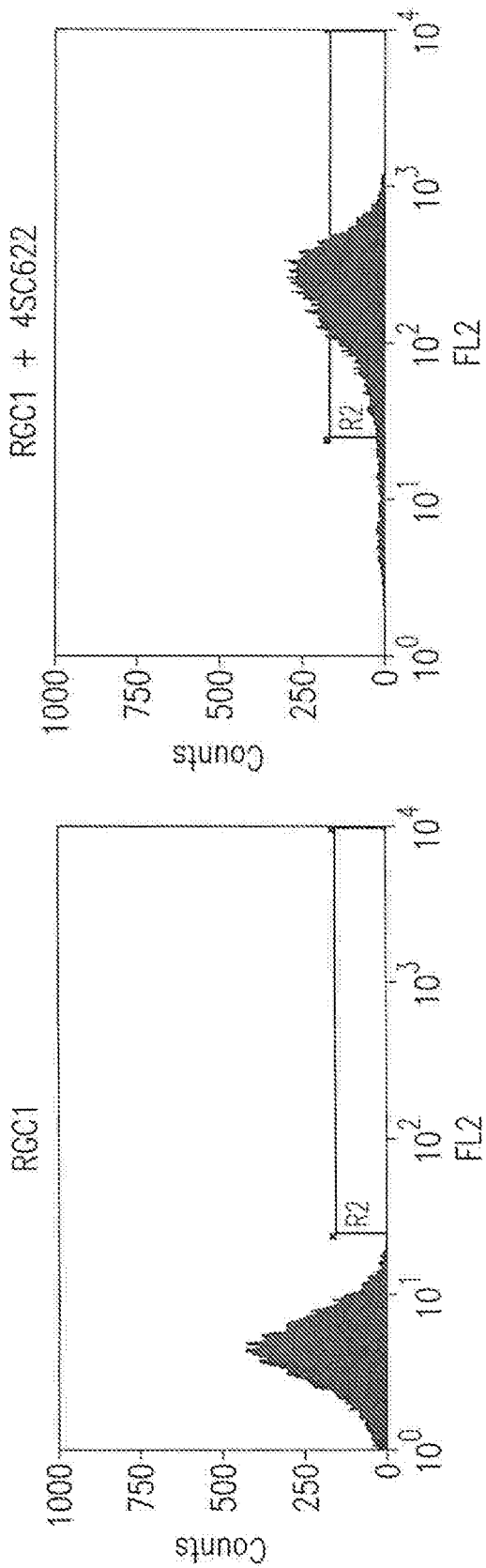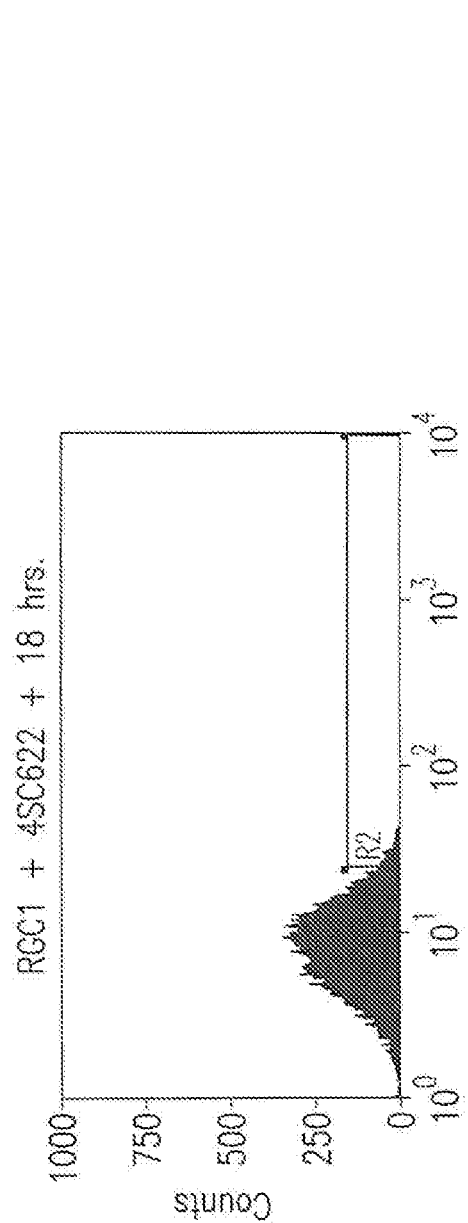

| Clone | Sp. Prod. | Clone | Sp. Prod. |
|---|---|---|---|
| 1A2 | 12.15 | 3A1 | 9.7 |
| 1A3 | 10.3 | 3B3 | 6.75 |
| 1B4 | 11.0 | 3B6 | 10.8 |
| 1C2 | 17.8 | 3C1 | 11.9 |
| 1D3 | 11.8 | 3C2 | 7.7 |
| 1D5 | 10.4 | 3C6 | 8.3 |
|  |  | 3D1 | 10.5 |

FIG.13

SEQUENCE LISTING

```
<160> NUMBER OF SEQ ID NOS: 14

<210> SEQ ID NO 1
<211> LENGTH: 195
<212> TYPE: PRT
<213> ORGANISM: Streptococcus

<400> SEQUENCE: 1

Thr Tyr Lys Leu Ile Leu Asn Gly Lys Thr Leu Lys Gly Glu Thr Thr
1               5                   10                  15

Thr Glu Ala Val Asp Ala Ala Thr Ala Glu Lys Val Phe Lys Gln Tyr
            20                  25                  30

Ala Asn Asp Asn Gly Val Asp Gly Glu Trp Thr Tyr Asp Asp Ala Thr
        35                  40                  45

Lys Thr Phe Thr Val Thr Glu Lys Pro Glu Val Ile Asp Ala Ser Glu
    50                  55                  60

Leu Thr Pro Ala Val Thr Thr Tyr Lys Leu Val Ile Asn Gly Lys Thr
65                  70                  75                  80

Leu Lys Gly Glu Thr Thr Thr Glu Ala Val Asp Ala Ala Thr Ala Glu
                85                  90                  95

Lys Val Phe Lys Gln Tyr Ala Asn Asp Asn Gly Val Asp Gly Glu Trp
            100                 105                 110

Thr Tyr Asp Asp Ala Thr Lys Thr Phe Thr Val Thr Glu Lys Pro Glu
        115                 120                 125

Val Ile Asp Ala Ser Glu Leu Thr Pro Ala Val Thr Thr Tyr Lys Leu
    130                 135                 140

Val Ile Asn Gly Lys Thr Leu Lys Gly Glu Thr Thr Thr Lys Ala Val
145                 150                 155                 160

Asp Ala Glu Thr Ala Glu Lys Ala Phe Lys Gln Tyr Ala Asn Asp Asn
                165                 170                 175

Gly Val Asp Gly Val Trp Thr Tyr Asp Asp Ala Thr Lys Thr Phe Thr
            180                 185                 190

Val Thr Glu
    195

<210> SEQ ID NO 2
<211> LENGTH: 96
<212> TYPE: PRT
<213> ORGANISM: Homo sapiens

<400> SEQUENCE: 2
```

```
Gln Val Leu Gly Leu Gln Leu Pro Thr Pro Val Trp Phe His Val Leu
1               5                   10                  15

Phe Tyr Leu Ala Val Gly Ile Met Phe Leu Val Asn Thr Val Leu Trp
            20                  25                  30

Val Thr Ile Arg Lys Glu Leu Lys Arg Lys Lys Lys Trp Asp Leu Glu
        35                  40                  45

Ile Ser Leu Asp Ser Gly His Glu Lys Lys Val Thr Ser Ser Leu Gln
    50                  55                  60

Glu Asp Arg His Leu Glu Glu Leu Lys Cys Gln Glu Gln Lys Glu
65                  70                  75                  80

Glu Gln Leu Gln Glu Gly Val His Arg Lys Glu Pro Gln Gly Ala Thr
                85                  90                  95

<210> SEQ ID NO 3
<211> LENGTH: 33
<212> TYPE: DNA
<213> ORGANISM: Artificial Sequence
<220> FEATURE:
<223> OTHER INFORMATION: Synthetically generated oligonucleotide

<400> SEQUENCE: 3
cgggctgatg ctgcaccaac tgtatccatc ttc                              33

<210> SEQ ID NO 4
<211> LENGTH: 33
<212> TYPE: DNA
<213> ORGANISM: Artificial Sequence
<220> FEATURE:
<223> OTHER INFORMATION: Synthetically generated oligonucleotide

<400> SEQUENCE: 4
acactctccc ctgttgaagc tcttgacaat ggg                              33

<210> SEQ ID NO 5
<211> LENGTH: 31
<212> TYPE: DNA
<213> ORGANISM: Artificial Sequence
<220> FEATURE:
<223> OTHER INFORMATION: Synthetically generated oligonucleotide

<400> SEQUENCE: 5
gccaaaacaa cagcccccatc ggtctatcca c                               31

<210> SEQ ID NO 6
<211> LENGTH: 35
<212> TYPE: DNA
<213> ORGANISM: Artificial Sequence
<220> FEATURE:
<223> OTHER INFORMATION: Synthetically generated oligonucleotide

<400> SEQUENCE: 6
tcatttaccc ggagtccggg agaagctctt agtcg                            35

<210> SEQ ID NO 7
<211> LENGTH: 47
<212> TYPE: DNA
<213> ORGANISM: Artificial Sequence
<220> FEATURE:
<223> OTHER INFORMATION: Synthetically generated oligonucleotide

<400> SEQUENCE: 7
gagagtacct gcgtcatgca gatgtgaaac tgcaggagtc tggccct               47
```

<210> SEQ ID NO 8
<211> LENGTH: 38
<212> TYPE: DNA
<213> ORGANISM: Artificial Sequence
<220> FEATURE:
<223> OTHER INFORMATION: Synthetically generated oligonucleotide

<400> SEQUENCE: 8
gagagacctg cgtcagctga ggagacggtg accgtggt                              38

<210> SEQ ID NO 9
<211> LENGTH: 35
<212> TYPE: DNA
<213> ORGANISM: Artificial Sequence
<220> FEATURE:
<223> OTHER INFORMATION: Synthetically generated oligonucleotide

<400> SEQUENCE: 9
gagagggtct cacagccaaa acaacagccc catcg                                 35

<210> SEQ ID NO 10
<211> LENGTH: 42
<212> TYPE: DNA
<213> ORGANISM: Artificial Sequence
<220> FEATURE:
<223> OTHER INFORMATION: Synthetically generated oligonucleotide

<400> SEQUENCE: 10
gagagggtct ccggccgctc atttacccgg agtccgggag aa                         42

<210> SEQ ID NO 11
<211> LENGTH: 40
<212> TYPE: DNA
<213> ORGANISM: Artificial Sequence
<220> FEATURE:
<223> OTHER INFORMATION: Synthetically generated oligonucleotide

<400> SEQUENCE: 11
gagagcgtct catgcagaca tccagatgac ccagtctcca                            40

<210> SEQ ID NO 12
<211> LENGTH: 40
<212> TYPE: DNA
<213> ORGANISM: Artificial Sequence
<220> FEATURE:
<223> OTHER INFORMATION: Synthetically generated oligonucleotide

<400> SEQUENCE: 12
gagagcgtct cacagcccgt tttatttcca gcttggtccc                            40

<210> SEQ ID NO 13
<211> LENGTH: 36
<212> TYPE: DNA
<213> ORGANISM: Artificial Sequence
<220> FEATURE:
<223> OTHER INFORMATION: Synthetically generated oligonucleotide

<400> SEQUENCE: 13
gagagggtct cagctgatgc tgcaccaact gtatcc                                36

<210> SEQ ID NO 14
<211> LENGTH: 48
<212> TYPE: DNA
<213> ORGANISM: Artificial Sequence
<220> FEATURE:
<223> OTHER INFORMATION: Synthetically generated oligonucleotide -continued

```
<400> SEQUENCE: 14
gagagggtct caggccgctc aacactctcc cctgttgaag ctcttgac            48
```

ISOLATING CELLS EXPRESSING SECRETED PROTEINS

CROSS-REFERENCE TO RELATED APPLICATIONS

This application is a continuation of U.S. patent application Ser. No. 14/885,460 filed Oct. 16, 2015, which is a continuation of U.S. patent application Ser. No. 14/565,767, filed Dec. 10, 2014, which is a continuation of U.S. patent application Ser. No. 13/738,349, filed Jan. 10, 2013, now U.S. Pat. No. 9,389,236, which is a continuation of U.S. patent application Ser. No. 12/240,541, filed Sep. 29, 2008, now abandoned, which is a continuation-in-part of U.S. patent application Ser. No. 11/434,403 filed May 15, 2006, now U.S. Pat. No. 7,435,553, which is a continuation of U.S. patent application Ser. No. 11/099,158 filed Apr. 5, 2005, now abandoned, which is a divisional of U.S. patent application Ser. No. 10/050,279 filed Jan. 16, 2002, now U.S. Pat. No. 6,919,183, which claims the benefit under 35 USC § 119(e) of U.S. Provisional Patent Application No. 60/261,999 filed Jan. 16, 2001, which applications are each herein specifically incorporated by reference in their entireties.

This application incorporates by reference in its entirety the Sequence Listing entitled "0790E-USO4_ST25.txt", containing 5.6 kilobytes of data and last modified on Aug. 19, 2019, in computer readable-format (CRF) and electronic .txt format, filed electronically herewith.

BACKGROUND

Field of the Invention

The field of this invention is a method for identifying and isolating cells that produce secreted proteins. More specifically, the method allows rapid isolation of high expression recombinant antibody-producing cell lines, or may be applied directly to rapid isolation of specific hybridomas.

Prior art methods for expressing a gene of interest (GOI) in a host cell are known. Briefly, an expression vector carrying the GOI is introduced into the cell. Following stable integration, standard methods for isolating high expression cells may involve collection of cell pools, hand-picking colonies from plates, isolation of single cells by limited dilution, or other methods known in the art. Pools or individual clones are then expanded and screened for production of the protein of interest (POI) by direct measurement of POI activity, by immunological detection of POI, or by other suitable techniques. These procedures are laborious, inefficient, expensive, and the number of clones that can be analyzed is usually limited to a few hundred.

The large degree of heterogeneity in protein expression by cells following stable integration requires that many individual clones be screened in an effort to identify the rare integration event that results in a stable, high expression production cell line. This requirement calls for methods that enable rapid identification and isolation of cells expressing the highest level of protein production. Moreover, the collection of clone pools, or hand-picked colonies, risks losing high expression cells, which often grow more slowly, to faster growing low expression cells. Therefore, a need exists for methods that allow rapid screening and isolation of individual cells capable of high level expression of a secreted POI.

Incorporation of flow cytometry into methods used for the isolation of stable expression cell lines has improved the capability of screening large numbers of individual clones, however, currently available methods remain inadequate for diverse reasons. Diffusion of the POI between cells of different characteristics was also a problem.

BRIEF SUMMARY

The present invention describes a high-throughput screening method for the rapid isolation of those cells that secrete protein by directly screening for the protein of interest (POI). This invention also allows for the convenient monitoring of POI expression on a single-cell basis during the manufacturing process. Furthermore, this technology can be directly applied to screening of antibody producing cells. The technology can also be directly applied to screening of cells producing modified T cell receptors, such as, for example, cells that produce soluble forms of T cell receptors.

In one aspect, the invention provides a method of detecting and isolating cells that produce a secreted protein of interest (POI), comprising: a) constructing a nucleic acid molecule that encodes a cell surface capture molecule capable of binding a POI; b) transfecting a cell expressing the POI with the nucleic acid molecule of step a); c) detecting the surface-displayed POI by contacting the cells with a detection molecule, where in the detection molecule binds the POI; and d) isolating cells based on the detection molecule.

In various embodiments, the protein of interest is a ligand, a soluble receptor protein, a growth factor, an antibody, an Fab, a single chain antibody (ScFv), or a fragment thereof. When the protein of interest is an antibody, the antibody is selected from the group consisting of IgM, IgG, IgA, IgD or IgE, as well as various subtypes of these. In a specific embodiment, the antibody is an anti-Dll4 or an anti-IL-6 receptor antibody.

In more specific embodiments, the protein of interest is a growth factor selected from the group consisting of Interleukin (IL)-1, IL-2, IL-4, IL-5, IL-6, IL-7, IL-9, IL-10, IL-13, IL-15, IL-16, IL-17, IL-18, IL-21, Ciliary Neurotrophic Factor (CNTF), erythropoietin, Vascular Endothelial Growth Factor (VEGF), angiopoietin 1 (Ang-1), angiopoietin 2 (Ang-2), TNF, Interferon-gamma, GM-CSF, TGFβ, and TNF Receptor.

In various embodiments, the protein of interest comprises a variable domain of a T cell receptor. In specific embodiments, the protein of interest is a soluble T cell receptor (sTCR), or a protein comprising a T cell receptor extracellular domain fused to an Fc (TCR-Fc), In a specific embodiment, the Fc is a human Fc. In various embodiments, the protein comprises a variable domain of a T cell receptor extracellular domain. In various embodiments, the protein comprises a variable domain and a constant region of a T cell receptor extracellular domain.

The nucleic acid that encodes the protein of interest may be from any source, naturally occurring or constructed through recombinant technology, and may be selected from a DNA library.

In various embodiments, the cell surface capture molecule is a ligand-specific receptor, a receptor-specific ligand, an antibody-binding protein, an antibody or antibody fragment, such as an ScFv, or a peptide. When the capture molecule is a peptide, the peptide may be isolated from a phage display library. In more specific embodiments, the capture molecule may be Ang1, And2, VEGF, Tie1, Tie2, VEGFRI (Flt1), VEGFRII (Flk1 or KDR), CNTF, CNTFR-α, cytokine receptor components, fusions of two or more cytokine receptor components, or a fragments thereof. When the capture molecule is an antibody-binding protein, the antibody-binding protein may be an Fc receptor, an anti-immunoglobulin antibody, an anti-immunoglobulin ScFv, Protein A, Protein L, Protein G, Protein H or functional fragments thereof.

In various embodiments where the protein of interest comprises a T cell receptor variable domain, the cell surface capture molecule comprises an Fc receptor or a membrane-associated antigen capable of being recognized by the variable domain of the T cell receptor.

In several embodiments, the methods of the invention further comprise a membrane anchor that serves to anchor the POI to the cell membrane, exposed to the outside of the cell, and thus functions as a cell surface capture molecule. In specific embodiments, the membrane anchor is a transmembrane anchor or a GPI link. The membrane anchor may be native to the cell, recombinant, or synthetic.

In various embodiments, the protein of interest comprises a T cell receptor variable region, and the cell surface capture molecule comprises a membrane-associated antigen. In a specific embodiment, the membrane-associated antigen is a recombinant fusion protein comprising an antigen capable of being recognized by the T cell receptor variable region fused to a membrane anchor wherein the antigen is associated with the cell surface. In a specific embodiment, the recombinant fusion protein comprises an antigen fused to a transmembrane anchor or a GPI link. In another specific embodiment, the cell surface capture molecule comprises a recombinant fusion protein comprising an membrane anchor and an antigen that is capable of binding to a major histocompatibility (MHC) molecule, including but not limited to, for example, tumor antigens and self proteins of transformed phenotype.

In further embodiments, a signal sequence is added to the amino terminus of a POI, such that the protein is transported to the cell surface, and functions as a cell surface capture molecule. The signal sequence may be native to the cell, recombinant, or synthetic.

In various embodiments, a blocking molecule which binds the cell surface capture molecule is added to reduce the diffusion of the POI from the expressing cell to a neighboring cell. In another embodiment, the diffusion of the POI from the expressing cell to a neighboring cell and its adherence to that cell is reduced by increasing the viscosity of the media.

The cell isolated by the methods of the invention may be an antibody-producing cell fused to an immortalized cell. In more specific embodiments, the antibody-producing cell is a B-cell or derivative thereof. A B-cell derivative may be a plasma cell, a hybridoma, a myeloma, or a recombinant cell.

In addition, the methods of the invention are useful for identification of B-cells and derivatives thereof, or hybridomas that express secreted antibodies of a desired specificity, affinity or isotype. The invention can also be used for isolation of cells that express desired levels of an antibody or antibody fragments.

Detection of the cells with the displayed POI may be accomplished through the use of any molecule capable of directly or indirectly binding the displayed POI. Such detection molecules may facilitate the detection and/or isolation of the cells displaying the POI. In one embodiment, two molecules that bind each other and are differentially labeled are utilized. The detection and/or isolation may be accomplished through standard techniques known in the art.

In another aspect, the invention features a method of detecting and isolating cells that produce a secreted protein of interest (POI), comprising: a) transfecting a cell with a nucleic acid that encodes a cell surface capture molecule, wherein the cell surface capture molecule is capable of binding the POI; b) transfecting the cell of a) simultaneously or subsequently with a second nucleic acid that encodes a POI wherein the POI is expressed and secreted; c) detecting the surface-displayed POI by contacting the cell with a detection molecule, which binds the POI; and d) isolating cells based on the detection molecule.

In another aspect, the invention features a method of detecting and isolating cells that produce a POI, comprising: a) detecting a cell that expresses a cell surface capture molecule in high yield; b) isolating and culturing the cell detected in (a); c) transfecting the cell in (b) with a nucleic acid that encodes a POI wherein such POI is secreted; d) detecting the surface-displayed POI by contacting the cells with a detection molecule which binds the POI; and e) isolating cells based on the detection molecule.

In another aspect, the invention provides a method of detecting and isolating cells that produce high levels of protein of interest (POI), comprising: a) transfecting cells with a nucleic acid that encodes such cell surface capture molecule capable of binding the POI, wherein the cell expresses the POI; b) detecting a cell from (a) that expresses said cell surface capture molecule in high yield; c) isolating and culturing a high yield cell; d) detecting the surface-displayed POI by contacting the cell with a detection molecule binds the POI; and e) isolating the detected cell.

In another aspect, the invention provides a method of detecting and isolating cells that produce high levels of an immunoglobulin, comprising: (a) transfecting cells with a nucleic acid that encodes a cell surface capture molecule capable of binding the immunoglobulin, wherein the cell expresses the immunoglobulin; (b) detecting a cell of (a) that expresses the surface capture molecule in high yield; (c) isolating and culturing the cell that expresses the surface capture molecule in high yield; (d) detecting the immunoglobulin on the surface of the isolated and cultured cell of step (c) with a detection molecule that binds the immunoglobulin; and (e) isolating the cell detected in step (d) that bears the detected immunoglobulin on its surface.

In another aspect, a method for detecting cells that produce a desired level of an affinity agent that comprises a T-cell receptor (TCR) variable region is provided.

In another aspect, a method for detecting cells that produce a desired level of a TCR-Fc is provided, comprising: (a) transfecting cells with a nucleic acid that encodes an Fc receptor capable of binding a TCR-Fc, wherein the cell expresses an antigen recognized by the TCR-Fc; (b) detecting a cell of (a) that expresses the TCR-Fc in high yield; (c) isolating and culturing the cell that expresses the TCR-Fc in high yield; (d) detecting the antigen on the surface of the isolated and cultured cell of step (c) with a detection molecule; and (e) isolating the cell detected in step (d) that bears the detected antigen on its surface.

In various embodiments, the TCR is selected from a human TCR and a rodent TCR such as a rat, mouse, or hamster TCR. In a specific embodiment the Fc is a human Fc. In another specific embodiment, the Fc is a human Fc and the Fc receptor is a high affinity human Fc receptor. In a specific embodiment, the high affinity human Fc receptor is a human FcγRI.

In various embodiments, the cell surface capture protein is surface-bound antigen. In a specific embodiment, the antigen is bound to the surface by fusion to a transmembrane domain or a GPI linker.

Other objects and advantages will become apparent from a review of the ensuing detailed description.

BRIEF DESCRIPTION OF THE FIGURES

FIG. 3 summarizes the ability of IgG from a variety of animal species to block 4SC622 from binding to RGC1 cells.

FIG. 4A shows a flow cytometry single parameter histogram of unstained RGC1 cells.

FIG. 4B shows a flow cytometry single parameter histogram of 4SC622 binding to FcγR1-expressing RGC1 cells as indicated by PE-AG184 binding.

FIG. 4C shows a flow cytometry single parameter histogram of rat IgG blocking the binding of 4SC622 to RGC1 cells as indicated by loss of PE-AG184 binding.

FIG. 7 summarizes a comparison of the specific productivities of 4SC622 expressing cell lines. CHO K1 transiently transfected with pEE14.1-622, hand-picked stable MSX-resistant clones of CHO K1 transfected with pEE14.1-622, and MSX-resistant 4SC622 production clones isolated after transfection of RGC1 cells with pEE14.1-622.

FIG. 8A shows a flow cytometry single parameter histogram of RGC1 cells stained with PE-AG184.

FIG. 8B shows a flow cytometry single parameter histogram of RGC1 cells incubated with 1 ug/ml 4SC622 for 1 hour prior to being stained with PE-AG184.

FIG. 8C shows a flow cytometry single parameter histogram of RGC1 cells that were incubated with 1 ug/ml 4SC622 for 1 hour, then incubated in medium without 4SC622 for 18 hours prior to staining with PE-AG184.

FIG. 13 summarizes the specific productivities of MSX-resistant stable clones of RGC10 cells transfected with pEE14.1-622

DETAILED DESCRIPTION

Figure 1:
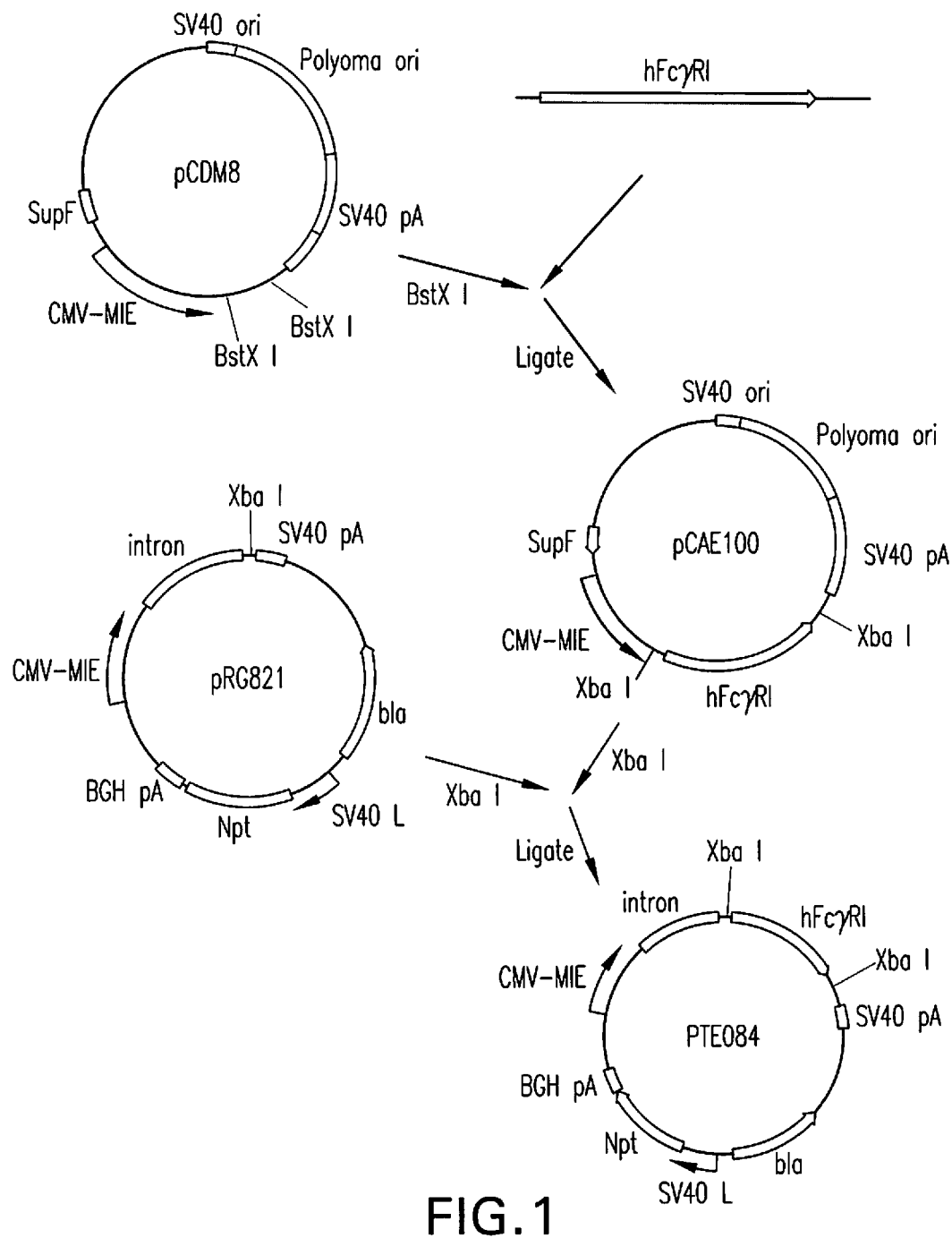
FIG. 1 represents the construction of pTE084, designed for the constitutive expression of human FcγRI from the upstream CMV-MIE promoter.

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only by the appended claims.

As used in this specification and the appended claims, the singular forms "a", "an", and "the" include plural references unless the context clearly dictates otherwise. Thus for example, a reference to "a method" includes one or more methods, and/or steps of the type described herein and/or which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to describe in their entirety.

General Description

The method of the invention provides substantial advantages over current methods for isolation and identification of protein-secreting cells. For example, cells that secrete antibodies may be rapidly and conveniently isolated based on desired specificity, avidity, or isotype. Furthermore, the amount of secreted protein produced may be directly quantified, unlike many methods in the prior art wherein production of secreted protein is indirectly quantified.

Recently, two additional methods that utilize flow cytometry have been developed for the high throughput isolation of stable high expression cell lines. The first method involves modification of the expression plasmid to include a transcriptional read out for the GOI mRNA. This is most often accomplished by inserting an internal ribosomal entry site (IRES) and a gene whose protein product is easily monitored by flow cytometry, most frequently green fluorescent protein (GFP), between the stop codon of the GOI and the terminal poly A site (Meng et al. (2000) Gene 242:201). The presence of an IRES allows the POI and GFP to be translated from the same mRNA. Therefore, the expression level of the GFP gene is indirectly related to the mRNA level for the GOI. Clones that accumulate the GFP at high levels are isolated by flow cytometry and then screened for POI production. Because this method depends on the coupling of GOI expression to the reporter gene by use of an IRES in a recombinant construction, it is not applicable to the isolation of hybridomas.

The use of flow cytometry in the isolation of expression clones allows for the rapid analysis of large numbers of clones in a high throughput format. Moreover, use of flow cytometry significantly reduces the direct handling of cells. Unfortunately, the level of GFP production is not a direct measure of the production level of the POI. Various mechanisms may uncouple the production of secreted POI from accumulation of GFP. Differences in production of the POI and the GFP reporter may result from differences in the translation efficiency of the two genes, secretion efficiency of the POI, or stability of the polycistronic mRNA.

Another method that uses flow cytometry to isolate expression clones involves encapsulation of cells within agarose microdrops (Weaver et al. (1990) Methods Enzymol. 2:234). In this method biotinylated antibodies specific for the POI are bound to the biotinylated agarose through streptavidin such that secreted POI is captured and retained within the microdrop (Gray et al., (1995) J. Immunol. Methods 182:155). The trapped POI is detected by immunostaining with an antibody specific for the POI. To reduce the encapsulating agarose from absorbing POI secreted from adjacent cells, the cells are placed in a low-permeability medium. Those cells with the highest antibody staining of the POI in the embedding agarose are identified and isolated by flow cytometry. The gel microdrop approach screens cells directly for their ability to secrete POI, rather than indirectly screening for expression of GOI mRNA, but requires the availability of suitable antibodies for trapping and staining the secreted POI and the procedure requires special equipment to generate the agarose gel microdrops. Moreover, some cells may be sensitive to the encapsulation process.

A variation of this method circumvents the requirement for embedding cells in a matrix by directly binding an antibody, specific for the POI, to the cell surface (Manz et al. (1995) PNAS 92:1921-1925). In this method, non-specific biotinylation of cell surface proteins with biotin-hydroxy-succinimide ester is followed by contact with a streptavidin-conjugated antibody capable of binding the POI. Cells secreting the POI become decorated with the POI which is then detected with an appropriately labeled second antibody. However, diffusion of POI between neighboring cells is problematic, and this method also requires a high viscosity medium to reduce diffusion of POI away from expressing cells. Because these high viscosity media are required for discriminating cells, the cells must be washed and placed in a medium suitable for cell sorting if so desired.

The problems associated with identification and isolation of high expression recombinant cell lines especially applies to the isolation of hybridomas that express an antibody of interest. However, the identification of useful hybridomas includes several additional problems; they must be screened first for antigen-binding activity, then for immunoglobulin isotype. Moreover, GFP-based methods are not applicable to the identification and isolation of hybridomas because construction of hybridomas does not include a recombinant construct such that expression of the antibody genes can be linked to a transcriptional reporter such as GFP. Hybridoma screening is a slow, laborious endeavor where the number of clones screened is limited by existing technologies.

The instant invention describes a novel and previously unknown method of identifying and isolating cells that produce secreted proteins. The invention is based on the production of a cell line that expresses a molecule, localized to the cell surface, which binds the POI. The cell surface-displayed POI can then be detected by labeling with various detection molecules. The amount of POI displayed on the cell surface, under specific conditions, is a direct measure of the total amount of POI secreted. POI producers may then be isolated from non-producers, and levels of production or POI characteristics may be differentiated. The advantage of the invention is that it directly quantifies the secreted POI rather than indirectly measuring the mRNA.

This invention relates to the construction or use of cells that express cell surface capture molecules which bind various secreted POIs in the same cell that produces the POI. As the cell secretes the POI, these cell surface capture molecules bind it, or complexes of POI and cell surface capture molecules may form intracellularly and then get secreted. Binding may occur in an autocrine manner or while being secreted. The cells that produce the secreted POI may then be identified and isolated. Such identification and isolation may be based on characteristics of the POI, production of the POI or lack thereof, or by specified levels of production. The cell surface capture molecule and/or the POI may be produced by the cell in its native state, or the cell surface capture molecules and/or the POI may be recombinantly produced. Through the construction or use of such a cell, any secreted protein may be captured by the cell surface capture molecule provided there is a corresponding affinity between the two. As explained further, any molecule may be manipulated such that it can be used as a cell surface capture molecule. Therefore, this invention may be utilized to isolate any cell that secretes a protein.

Most any protein has the capacity to function as a cell surface capture molecule as described by the invention. What is necessary is the ability of the desired protein to be anchored to the cell membrane and exposed to the extracellular space. If the desired cell has a signal sequence then only a membrane anchor, including but not limited to a transmembrane anchor or a GPI linkage signal, need be added to the cell surface capture molecule such that it remains anchored in the cell membrane exposed to the outside of the cell. Furthermore, if the desired protein lacks a signal sequence, a signal sequence may be added to the amino terminus of the desired protein, such that it is transported to the cell surface. A signal sequence and a membrane anchor may be native to the cell, recombinant, or synthetic.

Cells often secrete a wide variety of proteins, endogenously or following the introduction of recombinant DNA. Any secreted protein may be identified and the cell producing it may be isolated according to the method of this invention. Such secreted proteins include but are not limited to growth factors, growth factor receptors, ligands, soluble receptor components, antibodies, sTCRs, TCR-Fc's, and peptide hormones. Such secreted proteins may or may not be recombinant. That is, the secretion of some proteins of interest from the desired cell may not require the introduction of additional nucleotide sequences. For example, the secretion of antibodies from B-cells or plasma cells is not the result of introduction of recombinant nucleotide sequences into the B-cell or plasma cell. Recombinant secreted proteins may be produced by standard molecular biology techniques well known to the skilled artisan (see e.g., Sambrook, J., E. F. Fritsch And T. Maniatis. Molecular Cloning: A Laboratory Manual, Second Edition, Vols 1, 2, and 3, 1989; Current Protocols in Molecular Biology, Eds. Ausubel et al., Greene Publ. Assoc., Wiley Interscience, NY). These secreted proteins are useful for many commercial and research purposes. This invention encompasses the production of such secreted proteins through the methodologies of the invention. Detection of the cells with the displayed POI may be accomplished through the use of any molecule capable of directly or indirectly binding the displayed POI. Such detection molecules may facilitate the detection and/or isolation of the cells displaying the POI.

The invention is applicable to the isolation of, inter alia, a) ligand-producing cells by using the ligand-specific receptor as the cell surface capture molecule, b) soluble receptor-producing cells by using a surface bound receptor-specific ligand as the cell surface capture molecule, -c) antibody-producing cells by using an antibody-binding protein as the cell surface capture molecule, d) sTCR's by using an s-TCR-binding protein (e.g., and antigen recognized by the TCR) as the cell surface capture molecule, or e) TCR-Fc's, by using an Fc-binding protein as a cell surface capture molecule.

In accordance with the methodology of this invention, a cell is first transfected with a vector containing a nucleotide sequence that encodes a cell surface capture molecule that is capable of binding the secreted POI, under conditions in which such cell surface capture molecule is expressed. Transfected cells which are appropriate producers of such cell surface capture molecules are then detected and isolated, and such cells are cultured. These cells may either naturally produce the POI, or the POI may be recombinantly produced. If the cells naturally produce the POI, they are ready for detection and isolation. If the POI is to be recombinantly produced, then the isolated and cultured cells expressing the specified cell surface capture molecule are transfected with second nucleotide sequence that encodes the secreted POI, under conditions in which the secreted POI is expressed. Upon expression, the secreted POI binds to the cell surface capture molecules and the cells displaying bound POI are detected and isolated.

If the POI is naturally produced by the cell, the cell will not be transfected with nucleotide sequence encoding the POI. Therefore, this aspect of the invention is applicable to any and all cells producing a POI. In addition, if the cell surface capture molecule is naturally produced by the cell, the cell need not be transfected with nucleotide sequences encoding the cell surface capture molecule. Therefore, this aspect of the invention is applicable to any and all cells producing a cell surface capture molecule.

A wide variety of host cells may be transfected. These cells may be either of eukaryotic or of prokaryotic origin. The cells will often be immortalized eukaryotic cells, and in particular, mammalian cells, for example monkey kidney cells (COS), Chinese hamster ovary cells (CHO), HeLa cells, baby hamster kidney cells (BHK), human embryonic kidney cells (HEK293), leukocytes, myelomas, cell lines transfected with adenovirus genes, for example, AD5 E1, including but not limited to immortalized human retinal cells transfected with an adenovirus gene, for example, PER.C6™ cells, and embryonic stem cells. The cells may also be non mammalian cells including bacterial, fungi, yeast and insect cells, including, but not limited to, for example *Escherichia coli, Bacillus subtilus, Aspergillus* species, *Saccharomyces cerevisiae*, and *Pichia pastoris*. All cells may be grown in culture trays medium under appropriate conditions or in a synergistic host. The most desirable cells will be mammalian cells capable of culture.

The secreted POI bound to the cell surface capture molecule may be detected and isolated by various techniques known in the art. Cultures cells displaying the secreted POI may be contacted with (a) molecule(s) capable of directly or indirectly binding the secreted POI wherein such detection molecule(s) may contain a detection label, such as, for example, a chromogenic, fluorogenic, colored, fluorescent, or magnetic label. The label bound to the detection molecule may be detected and the cell isolated using various methods. Most preferably, within a cell population the label will be detected and the cell isolated utilizing flow cytometry. Alternatively, the detection molecule may be used for the direct isolation of cells displaying the POI. This may be accomplished by conjugation of the detection molecule to a culture plate, paramagnetic molecules, or any other particle or solid support. In addition, displayed POI may be detected directly by a property of the detection molecule or the POI.

In one embodiment, two detection molecules that bind each other and are differentially labeled are used to detect a displayed secreted POI that blocks that interaction. If a cell displays a secreted POI that binds the first detection molecule and blocks the interaction between the first and second detection molecule, that cell may be isolated based on the presence of only the first detection molecule on its surface. On the other hand, if a cell displays a secreted POI that binds the first detection molecule but does not block the interaction between the first and second detection molecule, that cell may be isolated based on the presence of both detection molecules on its surface. For example, antibody producing cells expressing antibodies that specifically block, or do not block, the formation of a receptor-ligand complex may be identified. If the detection molecules are a receptor and its ligand which are differentially labeled, then an antibody producing cell that expresses antibodies that block the receptor-ligand complex from forming may be detected by the presence of one label on its surface, whereas an antibody producing cell that expresses antibodies that do not block the receptor-ligand complex from forming may be detected by the presence of both labels on its surface.

In any of the embodiments and with regards to isolating expressing cells from non-expressing cells or lesser expressing cells, one of the principal difficulties, when the POI is a secreted protein, is diffusion of POI between neighboring cells. Therefore, it is critical that any system that is designed to capture the secreted POI on the cell surface must prevent the diffusion of the POI from the expressing cell to a neighboring cell and its adherence to that cell. If diffusion is allowed to occur, and neighboring cells become decorated with the secreted POI, then separation of cells based upon the degree of POI decoration will fail to discriminate high expressing cells from cells with low expression levels, and may fail to effectively isolate expressing from non-expressing cells.

Therefore one embodiment of this invention is to block the diffusion of the secreted POI between neighboring cells. This may be accomplished by the addition of a blocking molecule that binds either the cell surface capture molecule or the POI and prevents the binding of the secreted POI to the cell surface capture molecule. In this aspect, the detection molecules do not bind the blocking molecule. For example, if the cell surface receptor is the hFcγRI and the secreted POI possesses the human IgG Fc fragment, then diffusion of the secreted POI between neighboring cells may be blocked by the addition of exogenous rat IgG to the culture media. Detection of cells displaying secreted POI, and not bound rat IgG, is achieved by use of antibodies specific for human IgG Fc that do not recognize rat IgG. In another embodiment, binding of the secreted POI between neighboring cells is reduced by increasing the viscosity of the media.

In one embodiment of this invention, the secreted POI is not allowed to accumulate in the media. This may be accomplished by regulating the expression of the secreted POI and/or the cell surface capture molecule such that brief expression of the POI results in sufficient POI to bind the cell surface capture molecule but insufficient amounts for diffusion. In another embodiment, cells may be removed from the media containing accumulated POI, the POI bound to the cells is stripped off, and POI expression is allowed to continue for a limited period of time such that secreted POI does not accumulate in the media. Proteins may be stripped by methods known in the art, for example, washing cells with low pH buffer.

According to this invention, those cells in a cell population that bind the most detection molecules also express the most secreted POI. In fact, the more POI that an individual cell secretes, the more POI is displayed on the cell surface. This correlation between the amount of surface-displayed POI and the expression level of the POI in that cell allows one to rapidly identify cells with a desired relative expression level from a population of cells.

In one embodiment, a DNA library may be used to express secreted protein which may be displayed on the cell surface by the cell surface capture molecule. For example, a library of DNA may also be generated from the coding regions of the antibody variable domains from B-cells isolated from immunized animals. The DNA library may then be expressed in a cell that expresses a cell surface capture molecule specific for antibodies such that clones of desired specificity, isotype, or avidity may be identified and isolated by the method of the invention. In another embodiment, a library of DNA may be generated from the coding regions of T cell receptor variable domains from T-cells, and fused to, for example, an Fc capable of binding to an Fc-binding protein. The DNA library may them be expressed in a cell that expresses an Fc-binding protein such that clones of desired specificity, isotype, or avidity may be identified and isolated as described herein.

In another embodiment, transgenic mammals may be created that express a particular cell surface capture molecule in one or more cell types. The cells from such transgenic mammals may then be screened directly for the production of a POI. For example, it may be desirable to express a cell surface capture molecule, specific for antibodies, in plasma cells. Accordingly, plasma cells from immunized mice may be harvested and those cells producing antibodies specific to the desired antigen may be isolated by the method of the invention.

In a further embodiment of the invention, antibody production is measured through the use of a CHO cell line that expresses the human FcγR1 receptor (FcγRI) which binds the particular antibody or TCR-Fc that is the POI.

In another aspect of the invention, the protein of interest comprises one or more T cell receptor variable domains or a soluble T cell receptor. The one or more T cell receptor variable domains can be covalently linked to a moiety that can bind a cell surface capture protein. In a specific embodiment, the one or more T cell receptor variable domains are fused to an Fc sequence, e.g., a human Fc sequence, and the cell surface capture protein is an Fc receptor, e.g., an FcγR.

The general structures of TCR variable domains are known (see, e.g., Lefranc and Lefranc (2001) The T Cell Receptor FactsBook, Academic Press, incorporated herein by reference; see, e.g., pp. 17-20; see also, Lefranc et al. (2003) IMGT unique numbering for immunoglobulin and T cell receptor variable domains and Ig superfamily V-like domains, Developmental and Comparative Immunology 27:55-77, and Lefranc et al. (2005) IMGT unique numbering for immunoglobulin and T cell receptor constant domains and Ig superfamily C-like domains, Developmental and Comparative Immunology 29:185-203, each incorporated herein by reference). In one embodiment, a TCR variable domain of a TCR-Fc comprises an N-terminal region having a variable domain of 104-125 amino acids. In another embodiment, the TCR-Fc further comprises a TCR constant region comprising 91-129 amino acids. In another embodiment, the TCR-Fc further comprises a connecting peptide comprising 21-62 amino acids.

In one embodiment, the Fc sequence is fused directly or through a linker to the TCR variable domain. In another embodiment, the TCR-Fc comprises a TCR variable region and a TCR constant region, and the Fc sequence is fused directly or through a linker to the TCR constant region. In another embodiment, the TCR-Fc comprises a TCR variable region, a TCR constant region, and a connecting peptide, and the Fc sequence is fused directly or through a linker to the connecting peptide.

The sTCR, TCR-Fc, or fusion protein comprising one or more T cell receptor variable regions can be selected so as to specifically bind an antigen of interest, for example, a substance produced by a tumor cell, for example, tumor cell substance that is capable of producing an immune response in a host. In a specific embodiment, the antigen is an antigen that is present on the surface of a tumor cell (i.e., a tumor antigen), is recognized by a T cell, and that produces an immune response in a host. Tumor antigens include, for example, alphafetoprotein (AFP), carcinoembryonic antigen (CEA), MUC-1, epithelial tumor antigen (ETA), tyrosinase (e.g., for malignant melanoma), melanoma-associated antigen (MAGE), and mutated or abnormal forms of other proteins such as, for example, ras, p53, etc.

In one embodiment, the POI is a TCR-Fc, and the TCR-Fc comprises a TCR α chain variable region fused to an Fc sequence and a TCR β chain fused to the Fc sequence (each directly or through a linker), wherein the TCR α chain-Fc fusion and the TCR β chain-Fc fusion associate to form an αβ TCR-Fc. In a specific embodiment, the αβ TCR-Fc comprises the following two polypeptides: (1) a TCR α chain variable region fused to a TCR α chain constant region fused to an Fc sequence, and (2) a TCR β chain variable region fused to a TCR β chain constant region fused to an Fc sequence.

In another embodiment, the POI is a TCR-Fc having a TCR α variable region and a TCR β variable region and, optionally, a TCR α constant region and/or a TCR β constant region. In a specific embodiment, the TCR-Fc is encoded by a nucleic acid comprising (5' to 3') a TCR α variable region sequence, optionally followed by a TCR α constant region sequence, a TCR β variable region sequence, optionally followed by a TCR β constant region sequence, optionally a linker, then an Fc sequence. In a specific embodiment, the TCR-Fc is encoded by a nucleic acid comprising (5' to 3') a TCR β variable region sequence, optionally followed by a TCR β constant region sequence, a TCR α variable region sequence, optionally followed by a TCR α constant region sequence, optionally a linker, then an Fc sequence. In various embodiments, constructs encoding TCR-Fc's are preceded by signal sequences, e.g., secretion signal sequences, to render them secretable.

In another embodiment, the POI is a TCR-Fc, and the TCR-Fc comprises a TCR-Fc comprising a TCR γ chain fused to an Fc sequence and a TCR δ chain variable region fused to an Fc sequence to form a γδ TCR-Fc. In a specific embodiment, the γδ TCR-Fc comprises the following two polypeptides: a TCR α chain variable region fused to a TCR γ chain constant region fused to an Fc sequence, and (2) a TCR δ chain variable region fused to a TCR δ chain constant region fused to an Fc sequence.

T cell receptor variable regions can be identified and/or cloned by any method known in the art. The T cell receptor variable regions of the protein of interest are obtainable, for example, by expressing rearranged T cell receptor variable region DNA in a cell, for example, fused to a human Fc sequence. Rearranged T cell receptor variable regions specific for a particular antigen can be obtained by any suitable method known in the art (see references below), for example, by exposing a mouse to an antigen and isolating T cells of the mouse, making hybridomas of the T cells of the mouse, and screening the hybridomas with the antigen of interest to obtain a hybridoma of interest. Rearranged T cell variable regions specific for the antigen of interest can be cloned from the hybridoma(s) of interest. T cell receptor variable regions specific for an antigen can also be identified using phage display technology, for example, as provided in references below. The variable regions can then be cloned and fused, for example, to a human Fc to make a protein of interest that can bind to a cell surface capture molecule that is an FcγR.

Methods for identifying and/or cloning T cell receptor variable regions are described, for example, in U.S. Pat. No. 5,635,354 (primers and cloning methods); Genevée et al. (1992) An experimentally validated panel of subfamily-specific oligonucleotide primers (Vα1-w29/Vβ1-w24) for the study of human T cell receptor variable V gene segment usage by polymerase chain reaction, Eur. J. Immunol. 22:1261-1269 (primers and cloning methods); Gorski et al. (1994) Circulating T Cell Repertoire Complexity in Normal Individuals and Bone Marrow Recipients Analyzed by CDR3 Size Spectratyping, J. Immunol. 152:5109-5119 (primers and cloning methods); Johnston, S. et al. (1995) A novel method for sequencing members of multi-gene families, Nucleic Acids Res. 23/15:3074-3075 (primers and cloning methods); Pannetier et al. (1995) T-cell repertoire diversity and clonal expansions in normal and clinical samples, Immunology Today 16/4:176-181 (cloning methods); Hinz, T. and Kabelitz, D. (2000) Identification of the T-cell receptor alpha variable (TRAV) gene(s) in T-cell malignancies, J. Immunol. Methods 246:145-148 (cloning methods); van Dongen et al. (2002) Design and standardization of PCR primers and protocols for detection of clonal immunoglobulin and T-cell receptor gene recombinations in suspect lymphoproliferations: U.S. Pat. No. 6,623,957 (cloning methods and primers); Report of the BIOMED-2 Concerted Action BMH4-CT98-3936, Leukemia 17:2257-2317 (primers and cloning methods); Hodges et al. (2002) Diagnostic role of tests for T cell receptor (TCR) genes, J. Clin. Pathol. 56:1-11 (cloning methods); Moysey, R. et al. (2004) Amplification and one-step expression cloning of human T cell receptor genes, Anal. Biochem. 326:284-286 (cloning methods); Fernandes et al. (2005) Simplified Fluorescent Multiplex PCR Method for Evaluation of the T-Cell Receptor Vβ-Chain Repertoire, Clin. Diag. Lab. Immunol. 12/4:477-483 (primers and cloning methods); Li, Y. et al. (2005) Directed evolution of human T-cell receptors with picomolar affinities by phage display, Nature Biotech. 23/3: 349-354 (primers and cloning methods); Wlodarski et al. (2005) Pathologic clonal cytotoxic T-cell responses: nonrandom nature of the T-cell receptor restriction in large granular lymphocyte leukemia, Blood 106/8:2769-2780 (cloning methods); Wlodarski et al. (2006) Molecular strategies for detection and quantitation of clonal cytotoxic T-cell responses in aplastic anemia and myelodysplastic syndrome, Blood 108/8:2632-2641 (primers and cloning methods); Boria et al. (2008) Primer sets for cloning the human repertoire of T cell Receptor Variable regions, BMC Immunology 9:50 (primers and cloning methods); Richman, S. and Kranz, D. (2007) Display, engineering, and applications of antigen-specific T cell receptors, Biomolecular Engineering 24:361-373 (cloning methods). Examples of sTCRs are provided in, for example, U.S. Pat. Nos. 6,080,840 and 7,329,731; and, Laugel, B et al. (2005) Design of Soluble Recombinant T Cell Receptors for Antigen Targeting and T Cell Inhibition, J. Biol. Chem. 280:1882-1892; incorporated herein by reference. Fc sequences are disclosed herein; examples of Fc sequences, and their use in fusion proteins, are provided, for example, in U.S. Pat. No. 6,927,044 to Stahl et al. All of the foregoing references are incorporated herein by reference.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Construction of pTE084. pTE084 was constructed by ligating the 1,436 bp Xba I fragment from pCAE100 that encodes the human FcγRI (hFcγRI; GenBank accession number M21091) into the Xba I site of pRG821. The orientation of hFcγRI in desirable plasmids resulting from the ligation was examined by restriction mapping with Not I, Pst I, Eco RI, and Stu I. pTE084 was designed for the high level expression of hFcγRI, the high affinity cell surface receptor for the Fc domain of human IgG. It contains two independent expression cassettes. One cassette is a hFcγRI gene driven by the CMV-MIE promoter, and the second cassette is the neomycin phosphotransferase II (npt) gene, which confers resistance to G418, driven by the SV40 late promoter.

Figure 2A:
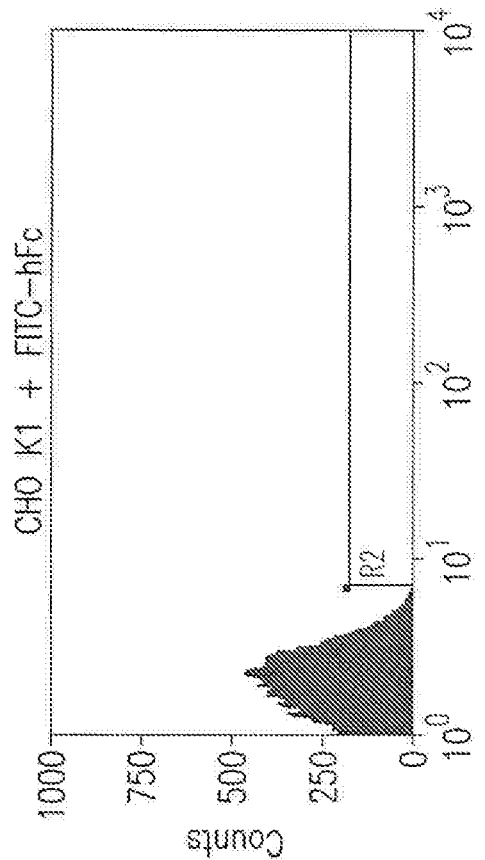
FIG. 2A shows a flow cytometry single parameter histogram of unstained CHO K1 cells.
Figure 2B:
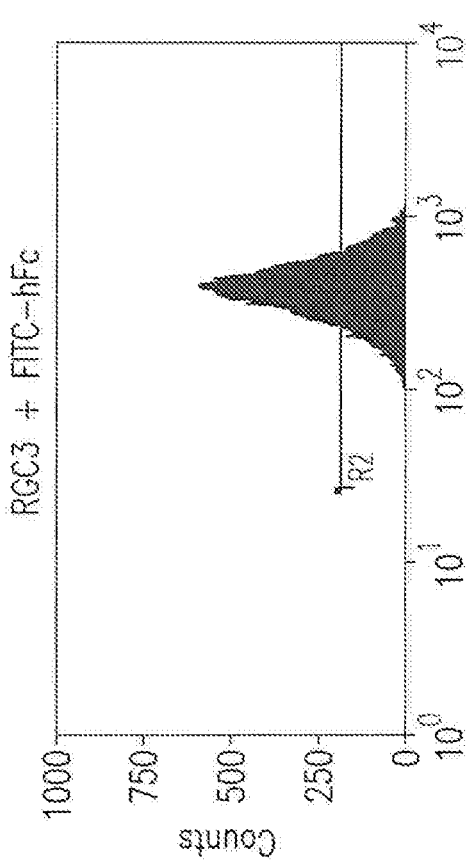
FIG. 2B shows a flow cytometry single parameter histogram of FITC-hFc stained CHO K1.
Figure 2C:
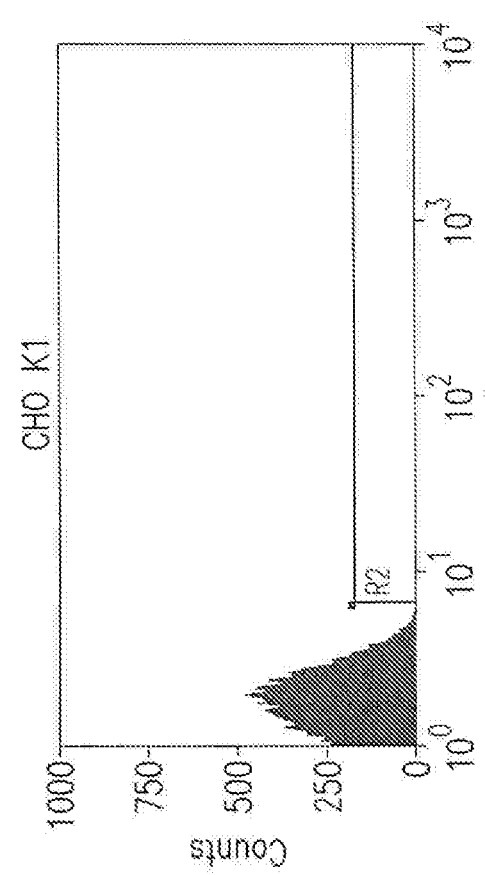
FIG. 2C shows a flow cytometry single parameter histogram of FITC-hFc stained G418-resistant CHO K1 cell pool after pTE084 transfection.
Figure 2D:
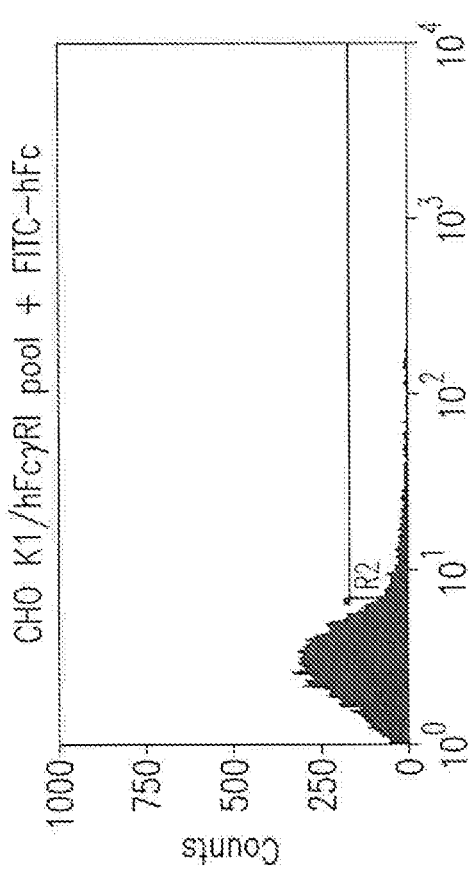
FIG. 2D shows a flow cytometry single parameter histogram of FITC-hFc stained RGC3 cells.

Construction of a CHO K1 derivative that expresses hFcγRI. CHO K1 cells ($4 \times 10^6$) were transfected with pTE084 using Lipofectamine™ (Life Technologies; Rockville, Md.) following manufacturer's suggestions. The cells were placed in the culture medium (10% fetal bovine serum, 90% Ham's F-12, 2 mM L-glutamine; all reagents were from Life Technologies, Rockville, Md.) containing 500 μg/ml G418 (Life Technologies) for 15 days. The cells that survived G418 selection were trypsinized, pooled, and stained with FITC-conjugated human IgG, Fc fragment (FITC-hFc; Jackson ImmunoResearch Laboratories, West Grove, Pa.). Briefly, the cells grown on 10 cm culture plates were washed once with Dulbecco's phosphate-buffered saline (PBS) without calcium chloride and magnesium chloride (Life Technologies). Three mls of 0.25% trypsin (Life Technologies) was added to each plate. The plates were swirled until the cells detached from the plate. Ten ml culture medium was immediately added to each plate of the detached cells. The cells were then collected by centrifugation at 1,000×g for 4 minutes. After removal of supernatant, the cells were resuspended in 4 ml of 2 μg/ml FITC-hFc diluted in culture medium. The cells were then placed on a platform shaker and stained for one hour at room temperature. To remove unbound FITC-hFc, the cells were washed twice with 20 ml PBS. The degree of FITC-hFc label on the cells was measured by flow cytometry on a MOFLO™ cell sorter (Cytomation; Fort Collins, Colo.). The FITC-hFc did not stain mock-transfected parental CHO K1 cells (FIGS. 2A and 2B) but gave rise to a distribution of fluorescence in the G418-resistant, pTE084-transfected pool (FIG. 2C). The top 1% most fluorescent cells from the selected pool were placed into 96-well plates at 1 cell/well by flow cytometry. Nine days later, 88 cell clones in the 96-well plates were expanded into 24-well plates. After 3 days, the cells in individual wells were washed once with 1 ml PBS, stained with 0.5 ml of 2 µg/ml FITC-hFc for 1 hour, washed twice with 1 ml PBS and examined for cell surface staining under a fluorescent microscope. The thirty three most fluorescent clones were chosen, expanded, then screened by flow cytometry (e.g., clone RGC3, as in FIG. 2D).

Diffusion of secreted protein between expressing cells and non-expressing cells among cells was blocked by adding IgG: As all cells in a hFcγRI clonal cell line express a cell surface hFcγRI, they all possess the ability to bind IgG or fusion proteins consisting of the Fc domain of IgG. Because hFcγRI binds IgG from a variety of species (van de Winkel and Anderson, 1991), a panel of animal IgGs was tested for the ability to block the binding of a protein containing a human IgG1 (hIgG1) Fc tag (4SC622) to hFcγRI-expressing cells. 4SC622 is a chimeric molecule consisting of IL-2Rγ extracellular domain fused to the hIL-4Rγ extracellular domain which is then fused to the hIG-1Fc domain. In this experiment, cultures of RGC1, a hFcγRI-expressing cell line selected from CHO K1 cells that have been stably transfected with pTE084, were incubated with 1 µg/ml 4SC622 for 18 hours in the presence or absence of 1 mg/ml IgG from different species in a 37° C. tissue culture incubator.

Cell surface binding of 4SC622 was determined by flow cytometry after washed cells were stained with phycoerythrin-conjugated mouse IgG1 monoclonal AG184 (PE-AG184) specific for the hIL-2Rγ component of 4SC622 (BD Pharmingen; San Diego, Calif.), following procedures outlined for cell staining with FITC-hFc.

Figure 5A:
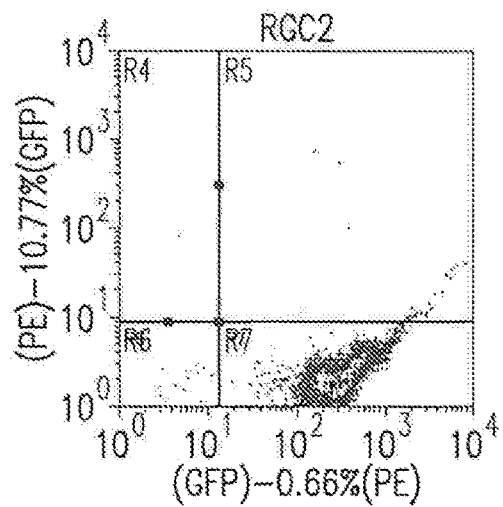
FIG. 5A shows a flow cytometry dual parameter histogram of RGC2 cells, which express the gene for hFcγRI and GFP, stained with PE-AG184.
Figure 5B:
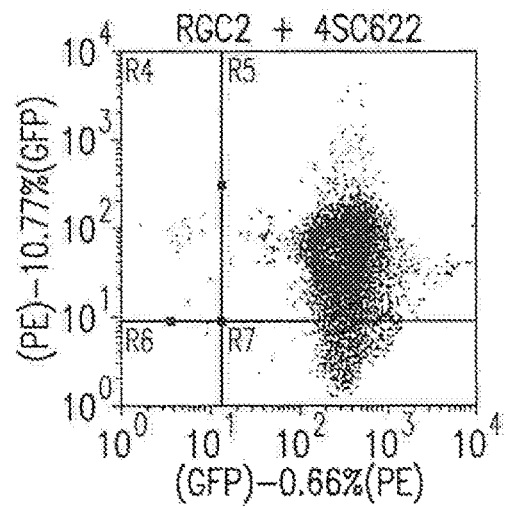
FIG. 5B shows a flow cytometry dual parameter histogram of RGC2 cells, which express the gene for hFcγRI and GFP, incubated with 1 ug/ml 4SC622 for 18 hours before being stained with PE-AG184.
Figure 5C:
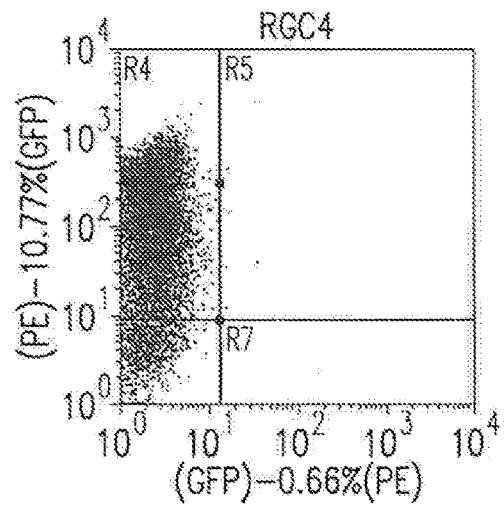
FIG. 5C shows a flow cytometry dual parameter histogram of RGC4 cells, which express the gene for hFcγRI and 4SC622, stained with PE-AG184.
Figure 5D:
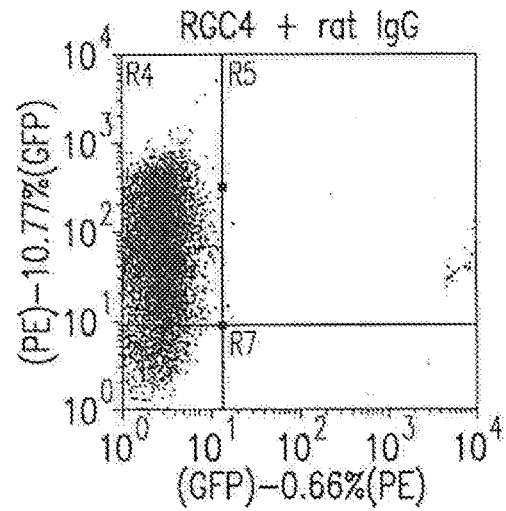
FIG. 5D shows a flow cytometry dual parameter histogram of RGC4 cells, which express the gene for hFcγRI and 4SC622, incubated with rat IgG (1 mg/ml) for 18 hours before being stained with PE-AG184.
Figure 5E:
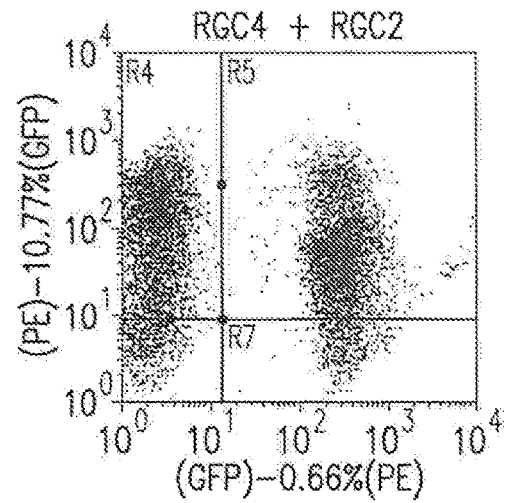
FIG. 5E shows a flow cytometry dual parameter histogram of a mixture of RGC2, which express the gene for hFcγRI and GFP, and RGC4 cells, which express the gene for hFcγRI and 4SC622, mixed and incubated together for 18 hours prior to staining with PE-AG184.
Figure 5F:
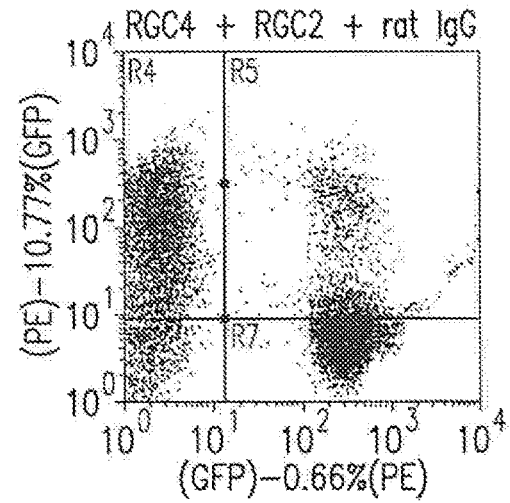
FIG. 5F shows a flow cytometry dual parameter histogram of a mixture of RGC2, which express the gene for hFcγRI and GFP, and RGC4 cells, which express the gene for hFcγRI and 4SC622, mixed and incubated together for 18 hours with 1 mg/ml rat IgG prior to staining with PE-AG184.

It was found that hIgG completely blocked 4SC622 from binding to the hFcγR1 expressed on the surface of RGC1 (FIG. 3). Rat, rabbit and canine-derived IgG also effectively blocked binding whereas bovine and ovine-derived IgG did not block. The ability of exogenously added rat IgG to block the binding of an exogenously added hIgG1 Fc-tagged protein (4SC622) to cell surface hFcγRI (FIG. 4) suggests that rat IgG can also block transfer between cells expressing a hIgG1 Fc-tagged protein at different levels. To test this, two cell lines that can be distinguished by the presence or absence of the green fluorescent protein (EGFP) were generated from RGC1. Briefly, to mark RGC1 cells with EGFP, $2 \times 10^6$ RGC1 cells were co-transfected with 0.5 mg PTE073 which encodes a hygromycin B phosphotransferase gene driven by phosphoglycerate kinase promoter, and 5 mg pRG816-EGFP which encodes EGFP gene driven by CMV-MIE promoter. The transfected cells were selected with 200 µg/ml hygromycin B (Sigma; St. Louis, Mo.) for two weeks. Green fluorescent cells were isolated by flow cytometry. One EGFP and hFcγRI-expressing clone, RGC2, was used in cell mixing experiments. The other cell line used in these experiments, RGC4, was generated by stable transfection of RGC1 with plasmid pEE14.1-622. pEE14.1-622 is a plasmid in which expression of 4SC622 is driven by the CMV-MIE promoter and includes a glutamine synthetase minigene, which confers resistance to the analog methionine sulfoximine (MSX), and allows for selection of stable integration events. RGC4 cells express hFcγRI on the cell surface and secrete the hIgG1 Fc-tagged protein 4SC622. One plate of mixed cells comprising 50% RGC2 and 50% RGC4 cells was incubated with 1 mg/ml rat IgG for 18 hours prior to staining with PE-AG184 then examined by flow cytometry. FIG. 5A shows the EGFP fluorescence of RGC2 cells, and RGC2 cells also bind exogenously added 4SC622 (1 µg/ml) as indicated by an increase in PE-AG184 fluorescence (FIG. 5B). RGC4 did not fluoresce in the EGFP gate (FIG. 5C). Significantly, exogenously added rat IgG did not reduce the percentage of RGC4 cells that stained positive for cell surface 4SC622 (FIG. 5D), suggesting that the binding of 4SC622 to hFcγRI occurred while the proteins were in transit to the cell surface. When RGC2 and RGC4 cells were mixed (FIG. 5E), the 4SC622 protein secreted from RGC4 cells accumulated in the medium and bound most of the RGC2 cells. However, the addition of 1 mg/ml rat IgG significantly reduced the percentage of RGC2 cells that bound 4SC622 (FIG. 5F), demonstrating that rat IgG blocked the transfer of secreted hIgG1 Fc-tagged protein from expressing cells to non-expressing cells.

Example 2: Cell Surface Fluorescence Correlates with the Expression Level of 4SC622

Figure 6:
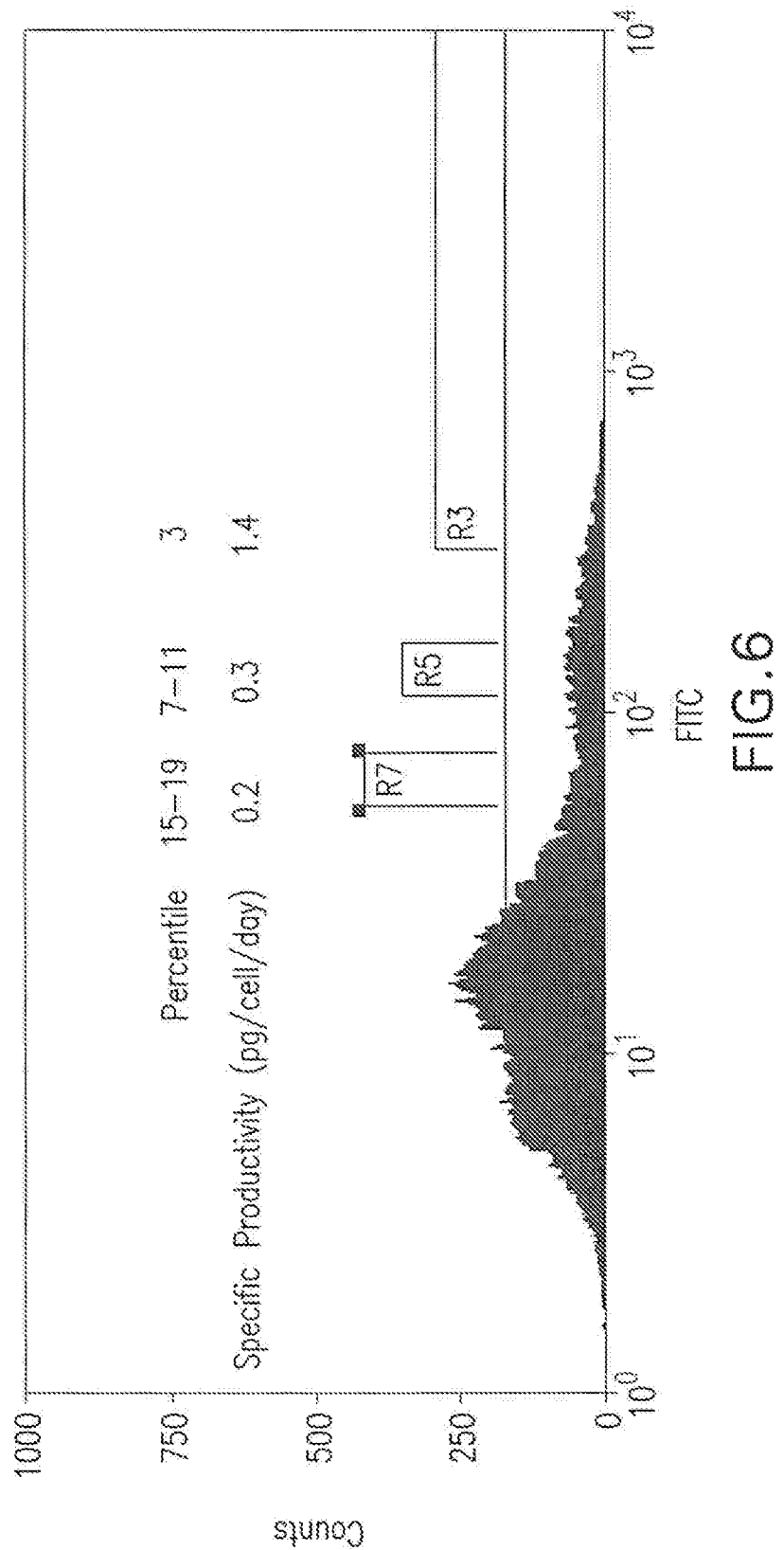
FIG. 6 shows a flow cytometry single parameter histogram of a MSX-resistant pool of RGC1 cells transfected with pEE14.1-622. Cells in the top 3% gate (R3), 7-11% gate (R5), and 15-19% gate (R7) were collected, expanded, and their 4SC622 productivity quantitated by immunostaining.

RGC1 cells ($4 \times 10^6$) were transfected with pEE14.1-622 and a pool of stable transfectants was obtained after selection for 2 weeks in medium comprised of 10% dialyzed fetal bovine serum, 90% glutamine-free Dulbecco's Modified Eagle's Medium (DMEM), 1×GS supplement, and 25 µM MSX (All reagents were from JRH Biosciences, Lenexa, Kans.). Rat IgG was added to the culture medium to 1 mg/ml 18 hours prior to immunostaining. The cells were trypsinized, washed with PBS, and stained with 1.5 µg/ml of a polyclonal FITC-conjugated anti-human IgG (H+L) F(ab')$_2$ fragment (Jackson ImmunoResearch Laboratories) for one hour at room temperature following procedures as described for FITC-hFc staining in Example 1. Cell staining was then analyzed by flow cytometry. The distribution of fluorescence suggested that the selected pool contained cells with a wide range of 4SC622 expression levels (FIG. 6). Cells in the top 3% (R3 bracket), 7-11% (R5 bracket), and 15-19% (R7 bracket) with respect to their immunofluorescence were sorted into three distinct pools and expanded for 9 days. Average 4SC622 production per cell for the pools was determined by measuring cell numbers and 4SC622 levels in the media after 3 days growth by an immuno-based Pandex assay (Idexx; Westbrook, Me.) following the manufacturer's recommendations. In the Pandex assay, fluoricon polystyrene assay particles coated with goat anti-human IgG, g-chain specific antibody (Sigma) were used to capture 4SC622 from the medium, and a FITC-conjugated goat anti-human IgG, Fc specific (Sigma) was used to detect bead-bound 4SC622. Known amounts of purified 4SC622 were included in the assay for calibration. Cells in the top 3%, 7-11%, and 15-19% pool were found to produce 4SC622 at 1.42, 0.36, and 0.22 µg/cell/day, respectively. Thus, there was a correlation between cell surface 4SC622 staining and specific protein production. This result suggests that individual cells that express 4SC622 at high levels may be obtained by isolating cells that were stained brightest by the polyclonal FITC-conjugated anti-human IgG (H+L) F(ab')2 fragment.

Example 3: Isolation of Expression Clones in RGC1: IL-4 Trap

To directly demonstrate the efficiency in generating clonal cell lines with high level secreted protein production by our methodology, clonal 4SC622 producing cell lines were generated from RGC1. RGC1 cells ($4 \times 10^6$) were transfected with pEE14.1-622, and selected for two weeks with 25 μM MSX to obtain a pool of stable transfectants. MSX-resistant cells were pooled and incubated with 1 mg/ml human IgG for 18 hours, prior to staining with PE-AG184. Six cells from the top 5% gate, as determined by flow cytometry analysis of cell surface 4SC622 staining, were isolated and expanded. 4SC622 production from the six clonal lines was determined and compared to 4SC622 production from clones obtained by hand-picking selected colonies followed by dilution cloning and amplification. One RGC1-derived clone, RGC4, produced 4SC622 at 12 μg/cell/day (FIG. 7, or Table 1). This level is similar to that of the best 4SC622 producer isolated by hand-picking and analyzing 2,700 clones. Thus, compared with hand-picking colonies, the methodology outlined in this invention proves to be far more efficient in the screening and cloning of high producers.

VEGF Trap. Plasmids pTE080 and pTE081 encode the genes for VEGF Traps, hVEGFR1R2 and hVEGF-R1R3. hVEGF-R1R2 is a chimeric molecule consisting of the first Ig domain of hVEGFR1 fused to the second Ig domain of hVEGFR2 which is then fused to the hIg1FC domain. hVEGFR1R3 is a chimeric molecule consisting of the first Ig domain of hVEGFR1 fused to the second Ig domain of hVEGFR3 which is then fused to the hIg1FC domain. In these plasmids, the gene for the VEGF Trap is driven by the CMV-MIE promoter and a glutamine synthetase minigene, which confers resistance to MSX, is expressed for selection of stable integration events. RGC1 cells were transfected with either of these plasmids and grown in medium containing 25 μM MSX for 2 weeks to select for cells in which the plasmid has stably integrated. MSX-resistant cells were incubated with 0.1 μg/ml Ig2a and mouse IgG3 for 18 hours prior to staining with 1.5 μg/ml polyclonal FITC-conjugated anti-human IgG (H+L) F(ab')$_2$ fragment. Cell were stained for 1 hour then washed twice with PBS prior to flow cytometry. Single cells were sorted into 96-well tissue culture plates from the pool of cells whose fluorescence was among the highest 1%. The cells in individual wells were expanded and their productivities were determined by Pandex assays. RGC-derived clones expressing both hVEGFR1R2 and hVEGFR1R3 had higher specific productivities and were isolated by screening fewer clones as compared to the highest-expressing hand-picked MSX-resistant colonies. See Table 1.

TABLE I

SPECIFIC PRODUCTIVITY COMPARISON

|  |  | Hand-picked CHO K1 Stable Cell Lines | | RGC1-derived Stable Cell Lines | |
| --- | --- | --- | --- | --- | --- |
| Protein | Transient (μg/ml) | Sp. Prod. (pg/cell/day) | # clones screened | Sp. Prod. (pg/cell/day) | # clones screened |
| 4SC622 | 1.1 | 12 | 2700 | 12 | 6 |
| hVEGF-R1R2 | 33 | 68 | 190 | 77 | 62 |
| hVEGF-R1R3 | 27 | 5 | 100 | 22.6 | 42 |

Figure 9:
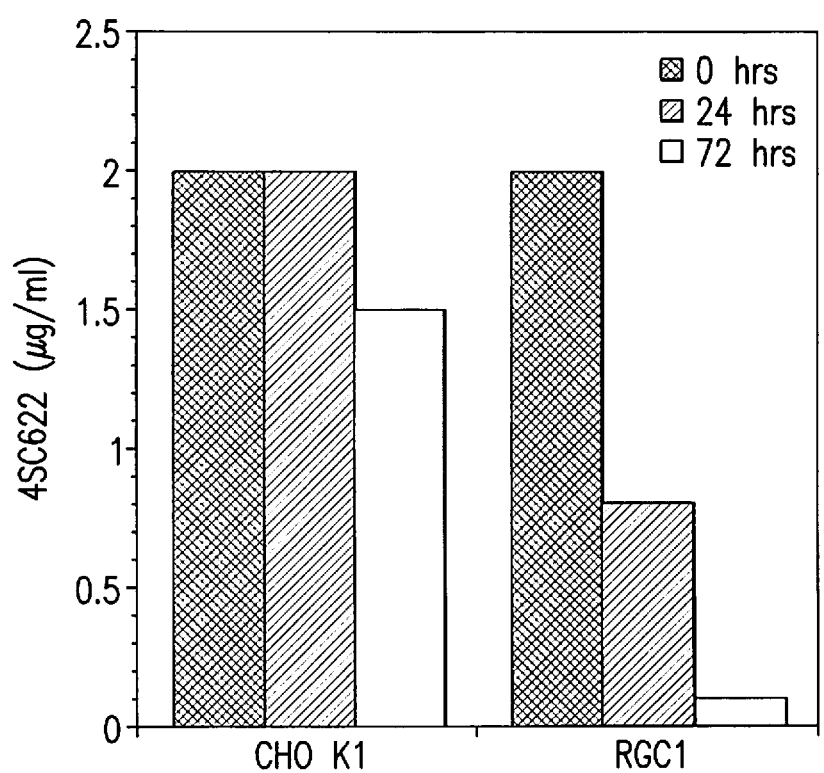
FIG. 9 shows that expression of the gene for hFcγRI results in loss of 4SC622 from the culture medium. RGC1 cells, or CHO K1 parental cells, were incubated in medium containing 2 ug/ml 4SC622. The concentration of 4SC622 remaining in the media was quantitated by immuno-staining after 24 hours, and 72 hours incubation.

Example 4: Cell Surface-Bound hIgG1 Fc-Tagged Protein is Internalized by RGC1 hFcγRI is known to induce internalization of its cell surface-bound ligand. To analyze whether RGC1 cells could internalize cell surface-bound 4SC622, 1 μg/ml 4SC622 was added to RGC1 cells for 1 hour and then the cells were immediately processed for 4SC622 immunostaining with PE-AG184 and flow cytometry analysis. Ninety-three percent of the cells stained positive for cell surface 4SC622 (FIG. 8B). Alternatively, 1 μg/ml 4SC622 was added to RGC1 cells for 1 hour, then the cells were washed and incubated in culture medium without 4SC622 with PE-AG184 for 18 hours. Flow cytometry analysis following immunostaining for 4SC622 showed that 9% of the cells retained 4SC622 on the cell surface (FIG. 8C). To further characterize the loss of surface-bound 4SC622, purified 4SC622 protein was added to the media of RGC1 and parental CHO K1 cells, then levels of 4SC622 in the media were measured over time. 4SC622, added to 2 μg/ml to the culture media in a 10 cm plate, was significantly lower in RGC1 conditioned medium after 3 days incubation as compared to the CHO K1 control (FIG. 9). These results show that the concentration of 4SC622 in the culture medium is reduced by the presence of hFcγRI on the cell surface. The results suggest that the depletion of 4SC622 from the media was the result of hFcγRI-4SC622 complex internalization. This internalization of receptor-ligand complexes may facilitate the effective removal of all 4SC622 from non-expressing cells in the presence of blocking IgG during the 18-hour blocking step.

Example 5: Construction of CHO K1 Cell Lines with Inducible hFcγRI Expression

Figure 10:
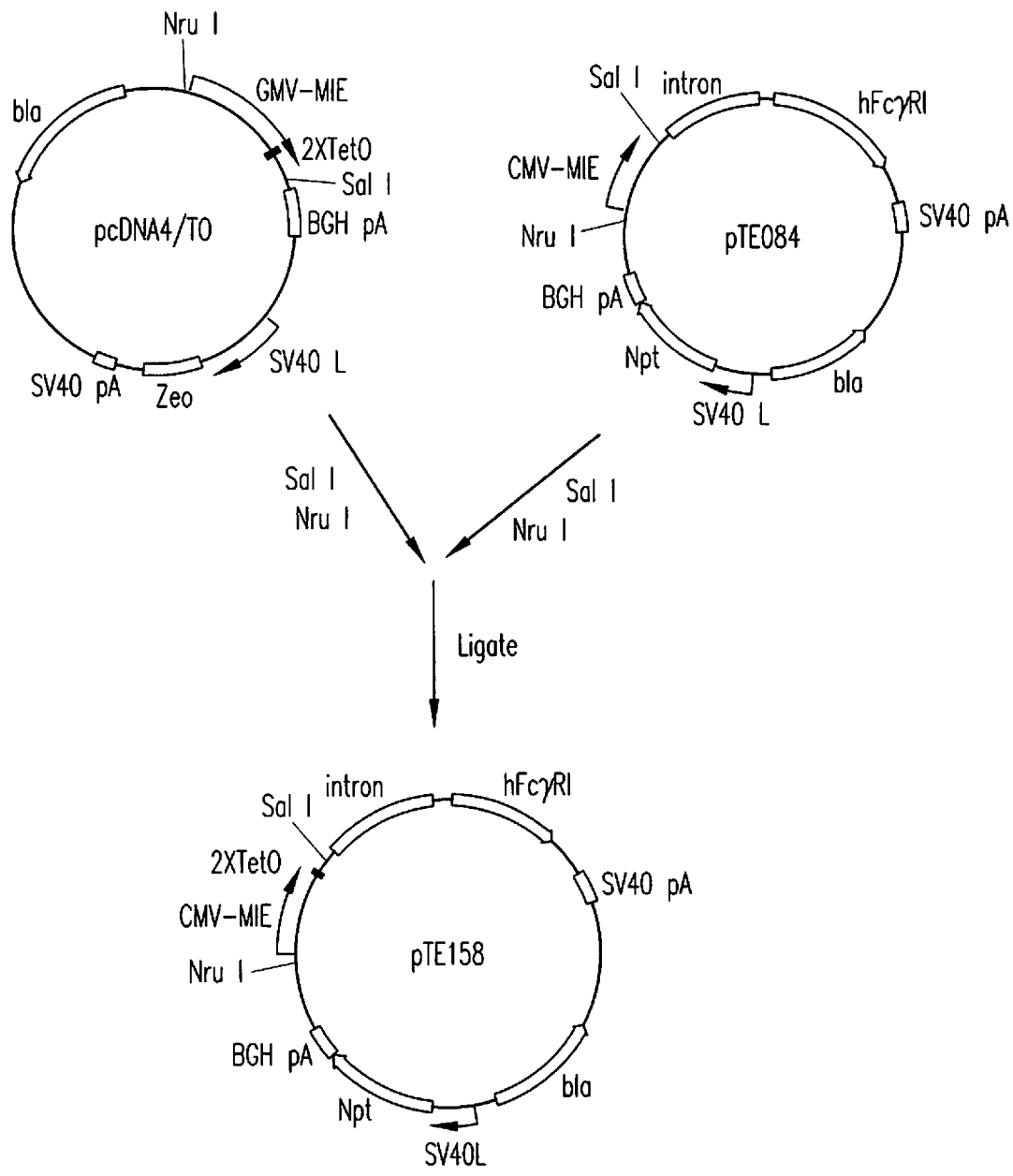
FIG. 10 represents the construction of pTE158, designed to allow TetR-regulated expression of human FcγRI. Two repeats of the tet operator sequence (TetO) are immediately downstream of the CMV promoter in pTE158.

Flow cytometry-based autologous secretion trap (FASTR) methods that utilize the hFcγRI allow rapid isolation of high expression clones. However, if hFcγRI mediates turnover of Fc-tagged proteins, then the realized production of the secreted protein by engineered hFcγRI expressing cells would be higher if hFcγRI expression could be inhibited during the production period. To this end, a CHO K1 cell line in which the expression of hFcγRI is induced by tetracycline, or the analog doxycycline, was constructed. In this system, CHO K1 cells were first engineered to express the tetracycline repressor protein (TetR) and hFcγRI was placed under transcriptional control of a promoter whose activity was regulated by TetR. Two tandem TetR operators (TetO) were placed immediately downstream of the CMV-MIE promoter/enhancer in pTE084 to generate pTE158 (FIG. 10). Transcription of hFcγRI from the CMV-MIE promoter in pTE158 was blocked by TetR in the absence of tetracycline or some other suitable inducer. In the presence of inducer TetR protein was incapable of binding TetO and transcription of hFcγRI occurs.

CHO K1 cells were transfected with pcDNA6/TR, a plasmid that confers resistance to blasticidin in which expression of TetR originates from the CMV-MIE promoter (Invitrogen; Carlsbad, Calif.). After two weeks of selection with 2.5 μg/ml blasticidin (Invitrogen), the stable transfectants were pooled. This pool was then transfected with pTE158, a plasmid that confers resistance to G418 in which the expression of hFcγRI is dependent on a CMV-MIE/TetO hybrid promoter. The cells consecutively transfected with pcDNA6/TR and pTE158 were selected with 400 μg/ml G418 and 2.5 μg/ml blasticidin for 12 days then pooled. The pool was induced for two days by the addition of 1 μg/ml doxycycline then stained with FITC-hFc to identify cells that express hFcγRI. The top 5% of cells expressing hFcγRI were collected as a pool, expanded for 6 days in the absence of doxycycline, and were again stained with FITC-hFc for the presence of hFcγRI. Cells that did not stain for hFcγRI were collected and expanded in culture medium containing 1 µg/ml of doxycycline for three days. The pool was then stained for the presence of hFcγRI and cells were isolated by flow cytometry. Cells that expressed the highest levels of hFcγRI (top 1%) were sorted onto 96 well plates at one cell per well. These cells presumably contained cell that had low non-induced expression levels of FcγR1 and high inducible levels of FcγR1. After expansion, the induction of hFcγRI by doxycycline in 20 clones was confirmed by immunostaining with FITC-hFc and flow cytometry. One clone was chosen for further characterization and was named RGC10.

Figure 11A:
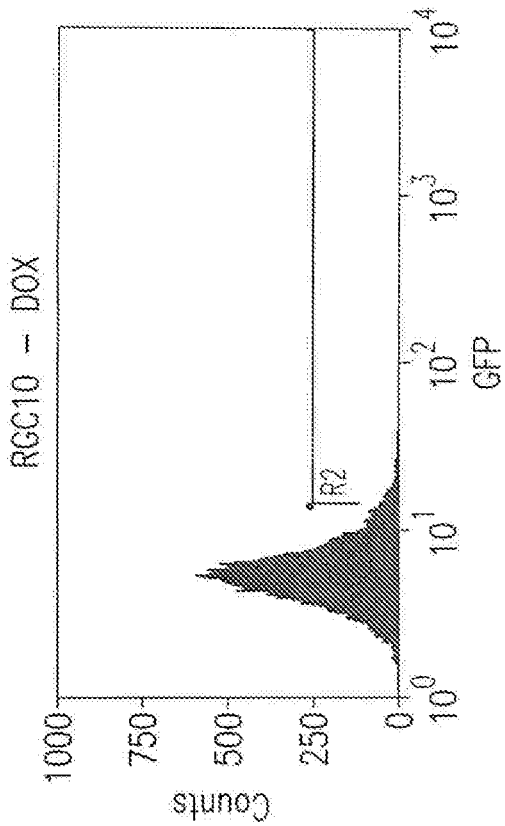
FIG. 11A shows a flow cytometry single parameter histogram of CHO K1 cells stained with FITC-hFc.
Figure 11B:
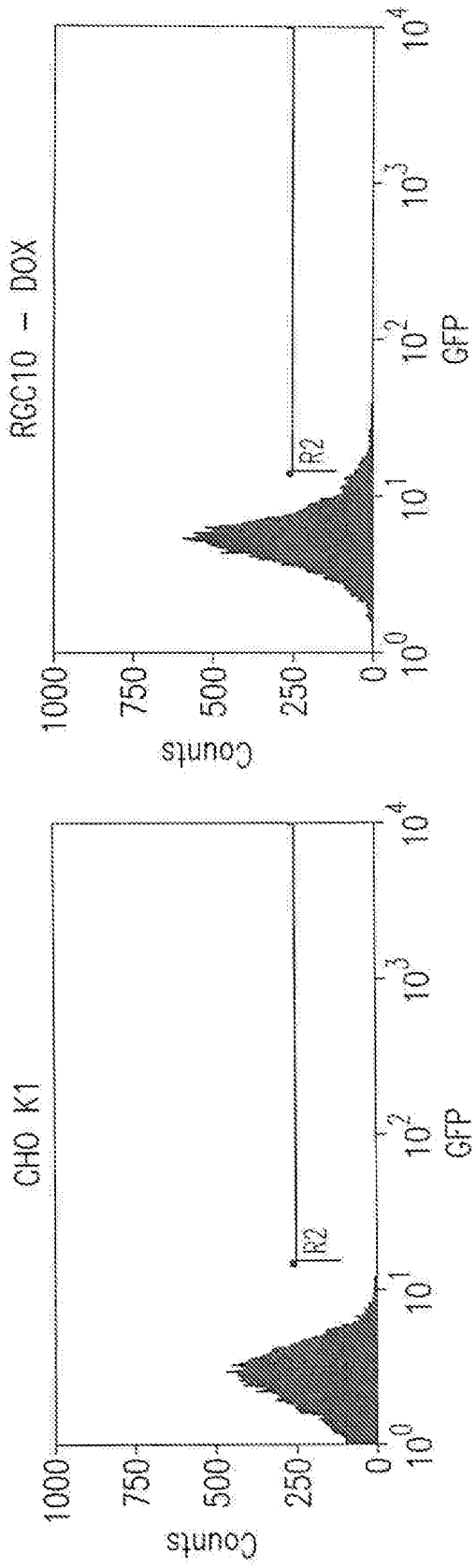
FIG. 11B shows a flow cytometry single parameter histogram of 10 RGC10 cells stained with FITC-hFc.
Figure 11C:
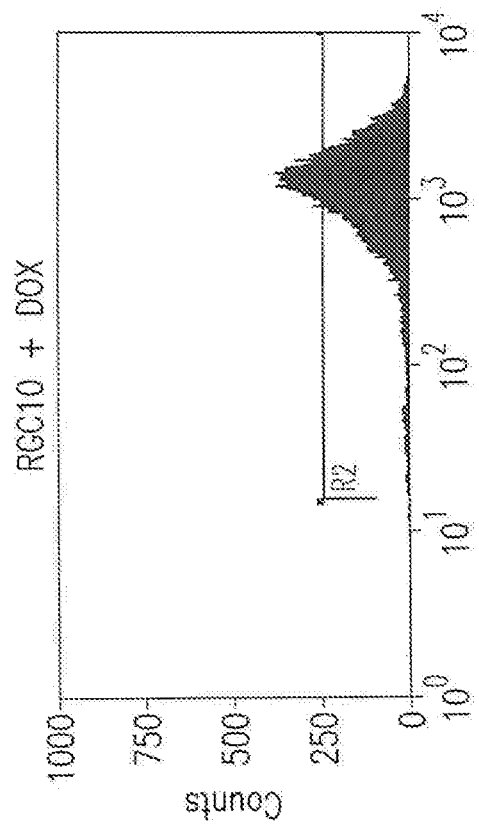
FIG. 11C shows a flow cytometry single parameter histogram of RGC10 cells induced with 1 ug/ml doxycycline for three days prior to staining with FITC-hFc.

In the absence of doxycycline, RGC10 did not express detectable levels of hFcγRI, whereas high levels of hFcγRI were observed in cells that were induced with 1 µg/ml of doxycycline for three days (FIG. 11). The mean fluorescence of RGC10 cells increased by more than 1,000 fold after induction by doxycycline.

Example 6: Isolation of 4SC622-Producing Cell Lines from RGC10

Figure 12A:
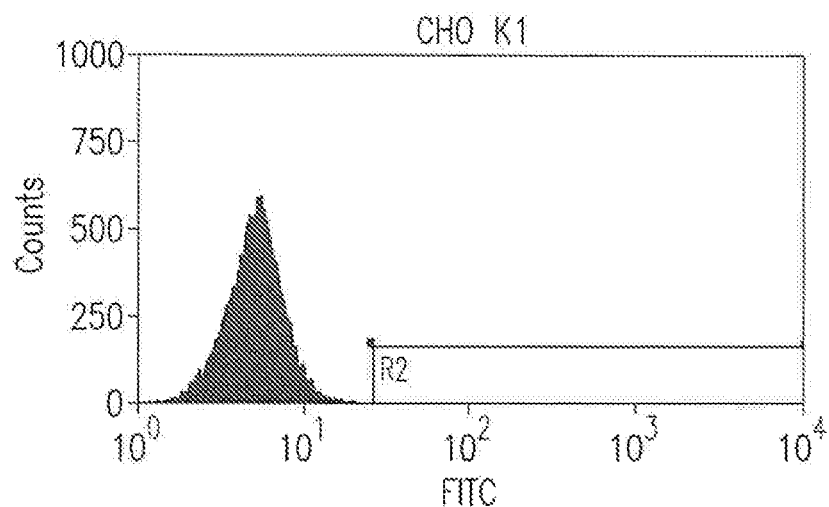
FIG. 12A shows a flow cytometry single parameter histogram of CHO K1 cells stained with polyclonal FITC-conjugated anti-human IgG (H+L) F(ab')$_2$ fragment.
Figure 12B:
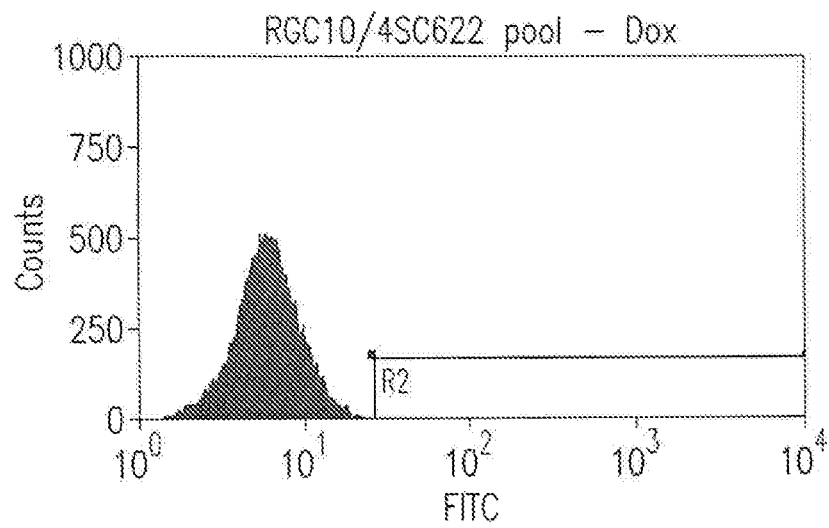
FIG. 12B shows a flow cytometry single parameter histogram of MSX-resistant RGC10 cells transfected with pEE14.1-622 and incubated with rat IgG (1 mg/ml) for 18 hours prior to staining with polyclonal FITC-conjugated anti-human IgG (H+L) F(ab')$_2$ fragment.
Figure 12C:
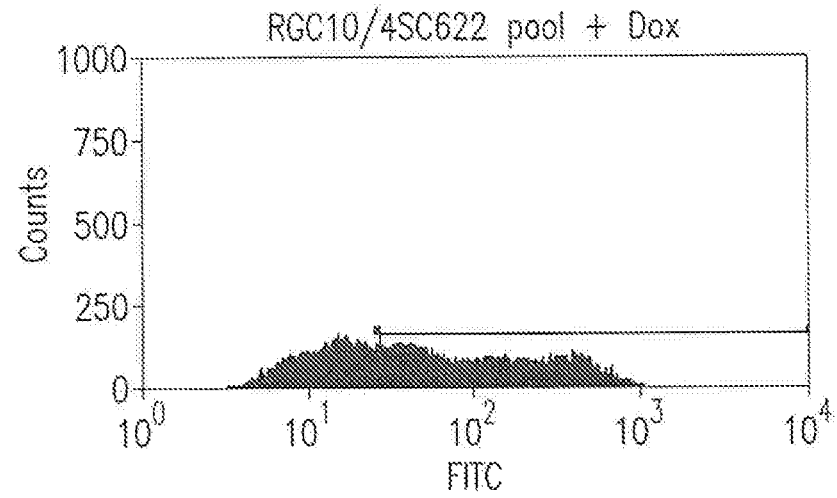
FIG. 12C shows a flow cytometry single parameter histogram of MSX-resistant RGC10 cells transfected with pEE14.1-622 induced with 1 ug/ml doxycycline for three days then incubated with rat IgG (1 mg/ml) for 18 hours prior to staining with polyclonal FITC-conjugated anti-human IgG (H+L) F(ab')$_2$ fragment.

RGC10 cells were transfected with pEE14.1-622, and MSX-resistant cells were pooled after selection with 25 mM MSX for two weeks. Expression of hFcγRI was induced by the addition of 1 µg/ml of doxycycline to the culture medium for three days. One mg/ml rat IgG was added to the culture medium containing doxycycline 18 hours prior to staining with polyclonal FITC-conjugated anti-human IgG (H+L) F(ab')2 fragment and analysis by flow cytometry. Cells that expressed the highest levels of 4SC622 (top 1%) were sorted into 96 well plates at 1 cell per well (FIG. 12C). Without induction of hFcγRI expression by doxycycline, staining with polyclonal FITC-conjugated anti-human IgG (H+L) F(ab')2 fragment fails to detect cell surface bound 4SC622 (FIG. 12B). Sixty clones were expanded in the absence of doxycycline. The specific productivity of the 13 highest producers was determined by Pandex assay (FIG. 13). The specific productivity of clone 1C2 was 17.8 µg/cell/day, significantly better than the 12 µg/cell/day observed for the best 4SC622 cell line previously isolated using the unregulated hFcγRI cell line RGC1.

Figure 14:
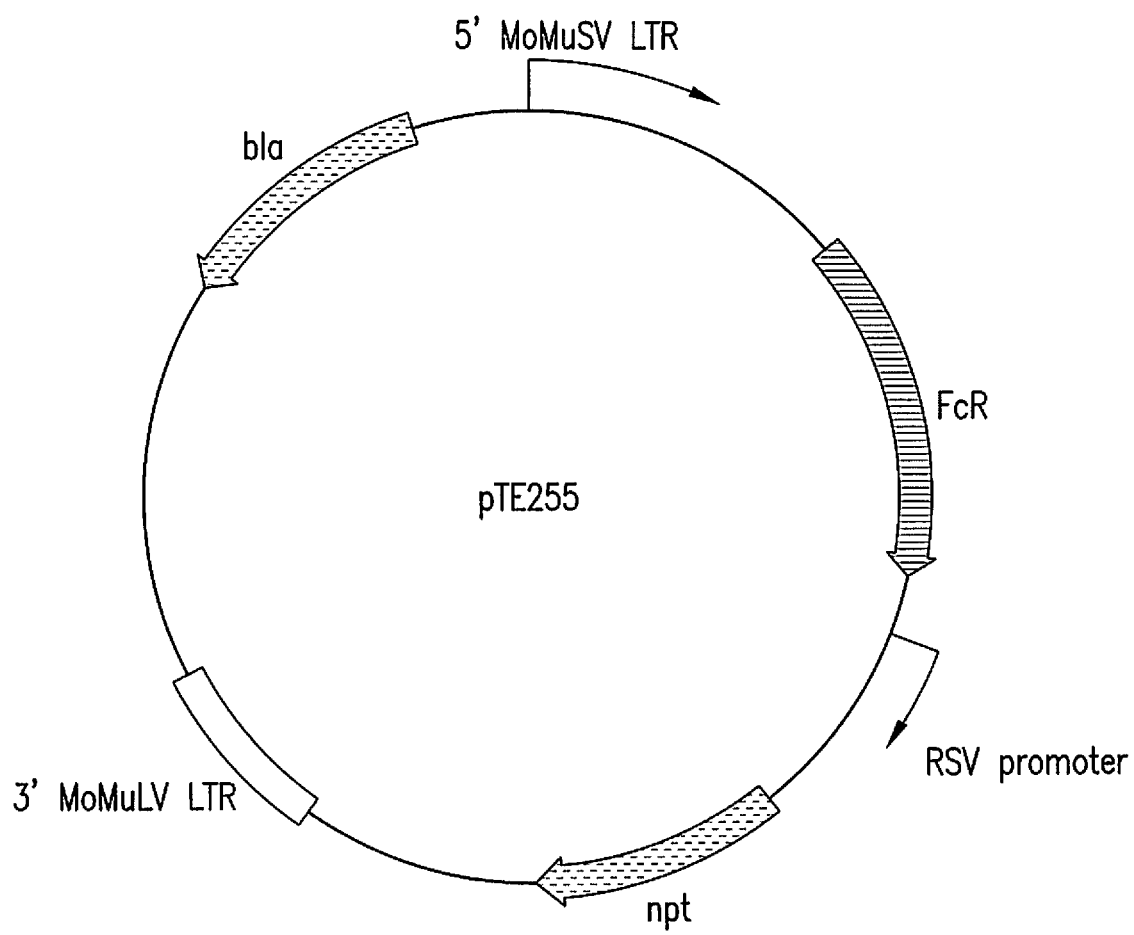
FIG. 14 represents the structure of pTE255, designed for the constitutive expression of human FcγRI from the upstream MoMuSV LTR promoter.
Figure 15A:
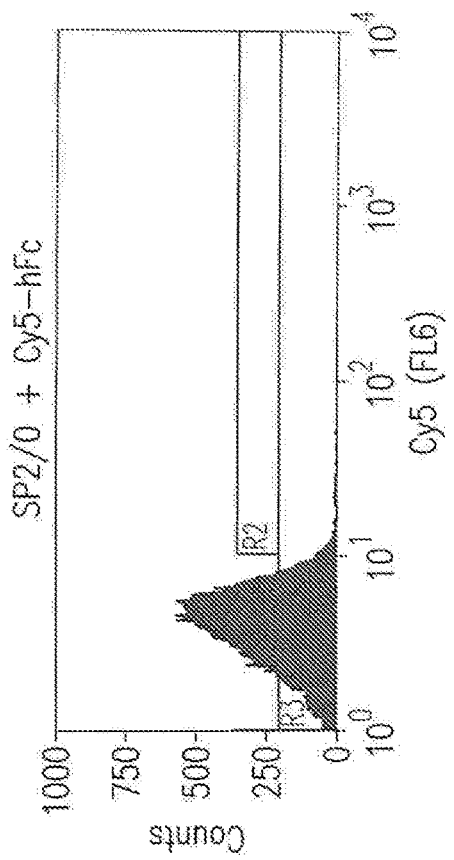
FIG. 15A shows a flow cytometry single parameter histogram of unstained Sp2/0 cells.
Figure 15B:
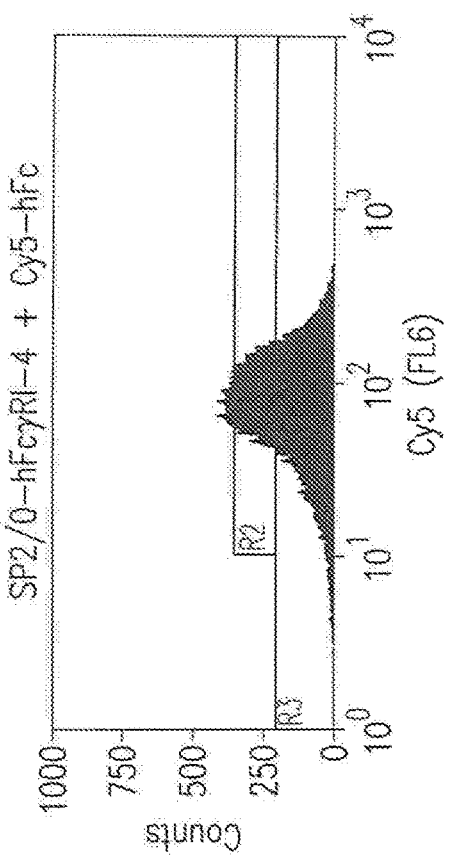
FIG. 15B shows a flow cytometry single parameter histogram of Cy5-hFc stained Sp2/0 cells.
Figure 15C:
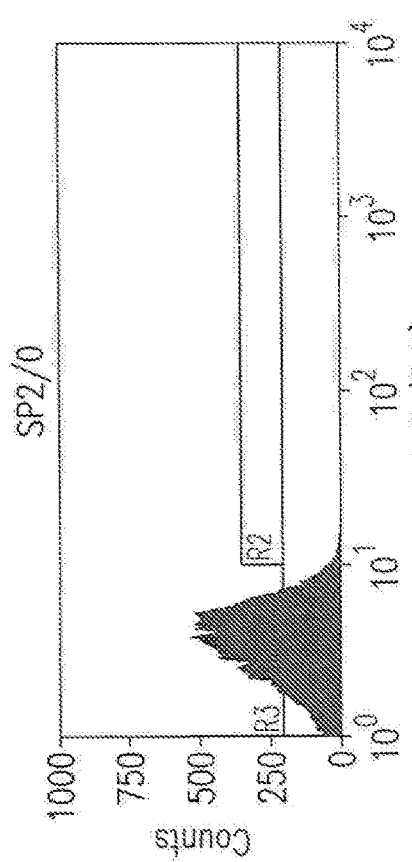
FIG. 15C shows a flow cytometry single parameter histogram of unstained Sp2/0-FcR-4 cells.
Figure 15D:
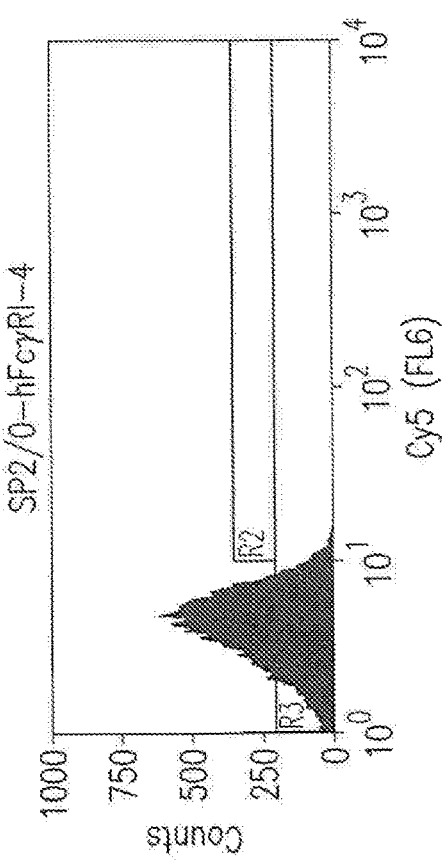
FIG. 15D shows a flow cytometry single parameter histogram of Cy5-hFc stained Sp2/0-FcR-4 cells.

Example 7: Sp2/0 Myeloma Cells can be Engineered to Express a Cell Surface Capture Protein In this example, the Sp2/0-Ag14 myeloma cell line was engineered to stably express hFcγRI to demonstrate that the autologous secretion trap method was applicable to cell lines other than CHO. The gene for hFcγRI was introduced into the myeloma cell by retroviral infection. The plasmid pLXRN (Clontech; Palo Alto, Calif.), a retroviral DNA vector wherein a gene of interest may be expressed from the upstream Moloney murine sarcoma virus long terminal repeat (MoMuSV LTR) promoter, was used to generate retrovirus encoding the hFcγRI gene. The 1,363 bp Xho I fragment from pTE084, encoding the human FcγRI gene, was cloned into the Xho I site of pLXRN. A plasmid in which hFcγRI cDNA expression was dependent on the MoMuSV LTR was chosen and named pTE255 (FIG. 14).

Pantropic retrovirus for the expression of hFcγRI was generated essentially following the manufacturer's guidelines. The packaging cell line GP-293, a HEK 293-based cell line that stably expresses the viral gag and pol proteins (Clontech; Palo Alto, Calif.), was co-transfected with 10 mg each of pVSV-G and pTE255. The plasmid pVSV-G allows expression of the viral envelope protein VSV-G that confers broad host range upon the infective particles.

Construction of Sp2-hFcγRI-4. The pantropic hFcγRI retrovirus was used to infect $1 \times 10^7$ Sp2/0-Ag14 myeloma cells (American Type Culture Collection; Manassas, Va.) at a multiplicity of about 10 infective particles per cell. Three days after infection, cells were stained for 1 hour then washed twice with PBS prior to analysis by flow cytometry. Those cells expressing hFcγRI, as indicated by bound FITC-hFc, were collected as a pool by flow cytometry. The pool was expanded for 13 days then again stained with FITC-hFc and cells expressing hFcγRI were collected as a pool by flow cytometry. These sorted cells were cultured in 10% fetal bovine serum 90% Dulbecco's Modified Eagle's Medium (DMEM) with 4.5 g/l glucose and 4 mM glutamine for 3 weeks, stained with FITC-hFc, and the cells with mean fluorescence in the top 1% of the population were cloned by single cell sorting. After expansion, 24 clones were examined by flow cytometry for expression of hFcγRI, as described above, and one clone, Sp2-hFcγRI-4, was chosen for additional characterization (FIG. 15).

Figure 16:
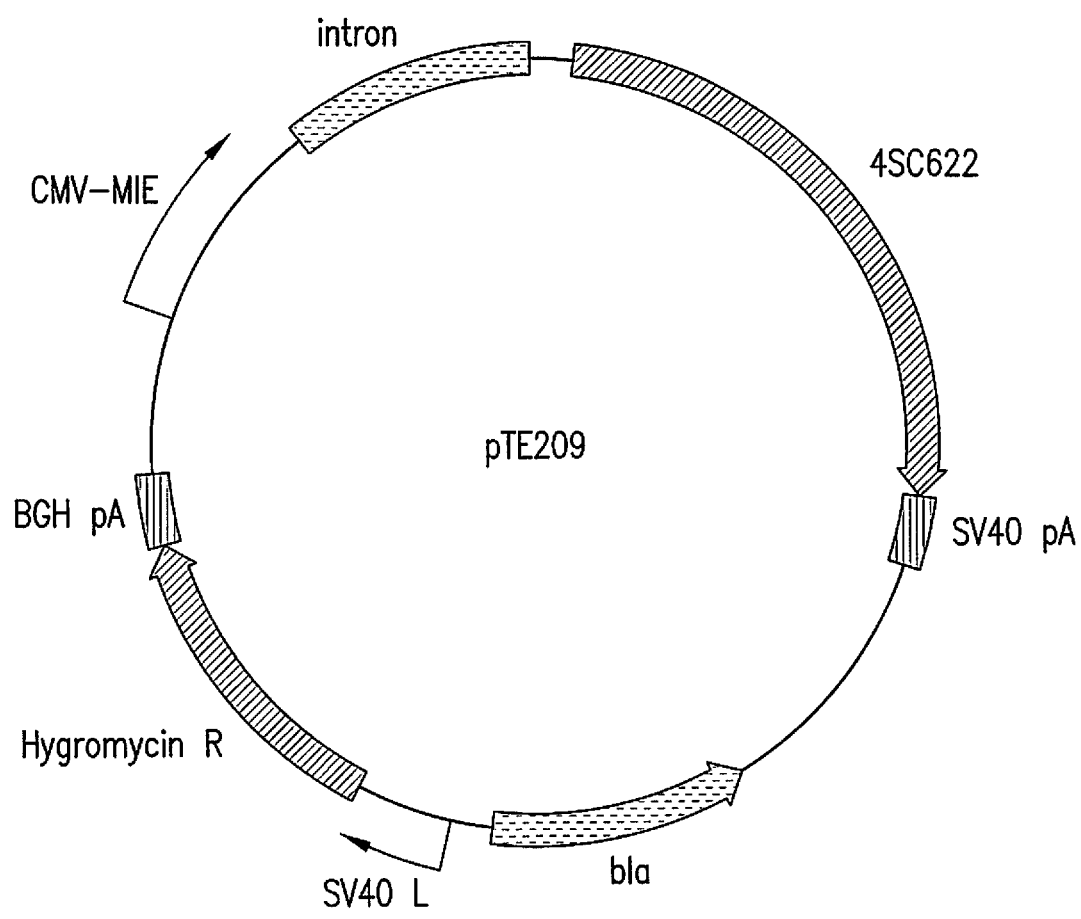
FIG. 16 represents the structure of pTE209, designed for the constitutive expression of 4SC622 from the upstream CMV MIE promoter.
Figure 17A:
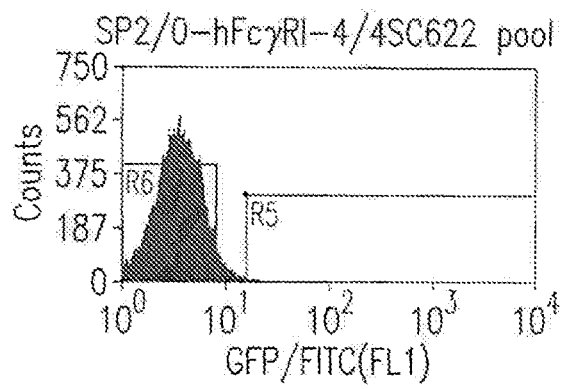
FIG. 17A shows a flow cytometry single parameter histogram of unstained hygromycin B-resistant Sp2/0-FcR-4 cells transfected with pTE209.
Figure 17B:
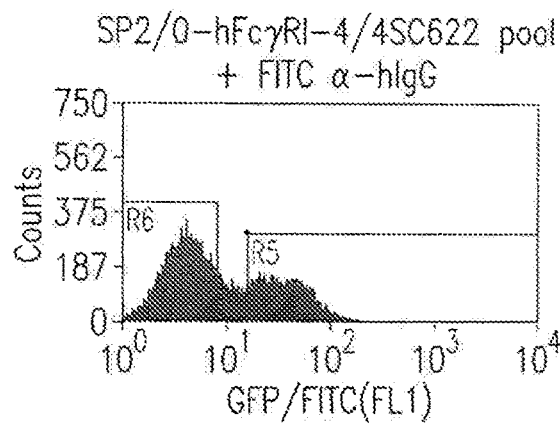
FIG. 17B shows a flow cytometry single parameter histogram of hygromycin B-resistant Sp2/0-FcR-4 cells transfected with pTE209 and incubated with rabbit IgG (1 mg/ml) for 18 hours prior to staining with polyclonal FITC-conjugated anti-human IgG (H+L) F(ab')$_2$ fragment.
Figure 17C:
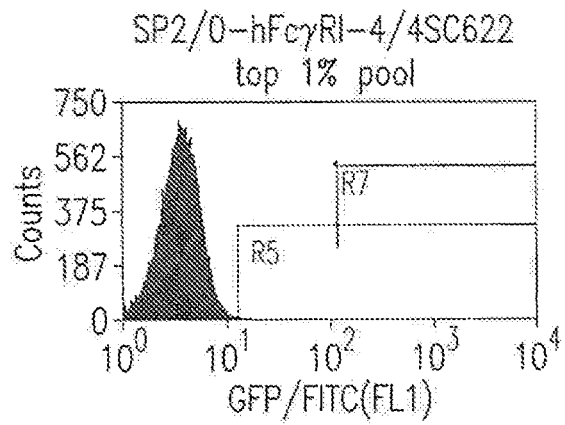
FIG. 17C shows a flow cytometry single parameter histogram of unstained cells expanded from the top 1% most fluorescent cells in FIG. 4B.
Figure 17D:
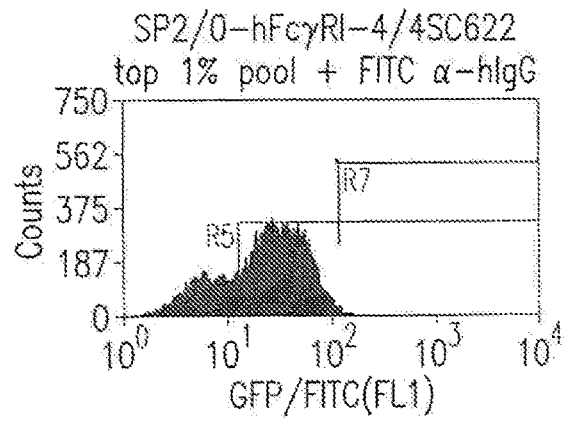
FIG. 17D shows a flow cytometry single parameter histogram of the cells expanded from the top 1% most fluorescent cells in FIG. 4B, incubated with rabbit IgG (1 mg/ml) for 18 hours prior to staining with polyclonal FITC-conjugated anti-human IgG (H+L) F(ab')$_2$ fragment.
Figure 17E:
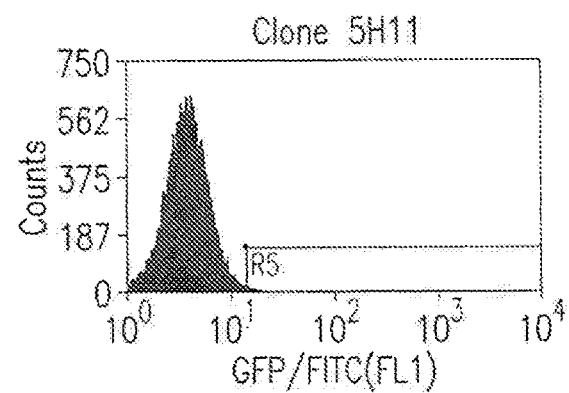
FIG. 17E shows a flow cytometry single parameter histogram of unstained clone 5H11 cells.
Figure 17F:
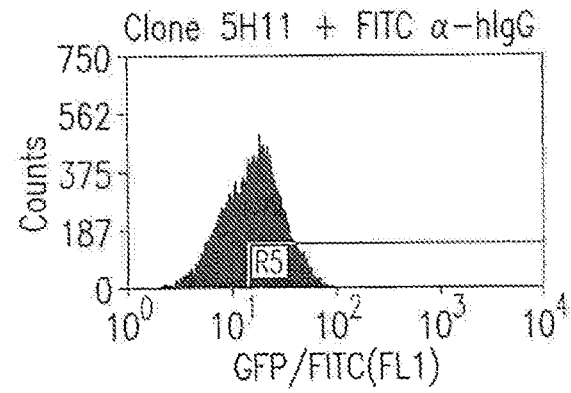
FIG. 17F shows a flow cytometry single parameter histogram of clone 5H11 cells incubated with rabbit IgG (1 mg/ml) for 18 hours prior to staining with polyclonal FITC-conjugated anti-human IgG (H+L) F(ab')$_2$ fragment.

Isolation of Sp2-hFcγRI-4 cells expressing 4SC622 protein. Sp2-hFcγRI-4 cells ($1 \times 10^7$) were transfected with pTE209 (FIG. 16), a plasmid that allows constitutive expression of 4SC622 from the CMV-MIE promoter and confers resistance to hygromycin. The transfected cells were placed in medium containing 10% FCS, 90% D-MEM and 400 µg/ml hygromycin for 14 days. Hygromycin-resistant cells were incubated with 1 mg/ml rabbit IgG for eighteen hours prior to staining with polyclonal FITC-conjugated anti-human IgG (H+L) F (ab')$_2$ fragment. Cells were stained for 1 hour then washed twice with PBS prior to analysis by flow cytometry. Labeled cells were collected as a pool by flow cytometry then cultured for 5 days and sorted as described above. Cells from the expanded pool that bound the most polyclonal FITC-conjugated anti-human IgG (H+L) F (ab')$_2$ fragment, top 1% population, were then cloned by single cell sorting (FIG. 17). Production of 4SC622 from ten clones was analyzed by ELISA and all 10 clones were found to express 4SC622; clone 5H11 produced 4SC622 at 0.5 µg per cell per day. These data showed that clones secreting 4SC622 were efficiently isolated by the autologous secretion trap method from a heterogeneous pool of cells derived from stable transfection of Sp2-hFcγRI-4 cells with pTE209.

To confirm that 4SC622 was autologously displayed on the surface of myeloma cells expressing both 4SC622 and hFcγRI, clone 5H11 was incubated with 1 mg/ml rabbit IgG for 18 hours then stained with FITC-conjugated anti-human IgG (H+L) F(ab')2 fragment and found to display cell surface 4SC622. Secreted protein was displayed under conditions in which cross-feeding was blocked by rabbit IgG, demonstrating the autologous display of 4SC622. These data indicated that the autologous secretion trap method described above was not limited to CHO cells and may be extended to myeloma and other cell types as well.

Figure 18:
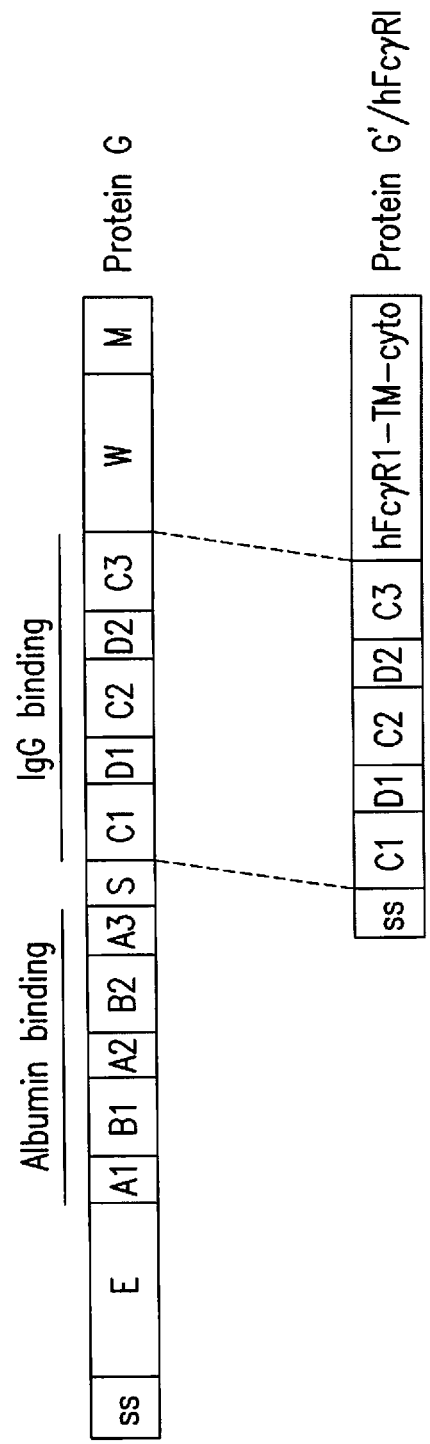
FIG. 18 shows schematic diagrams of domains of Protein G and Protein G/hFcγRI fusion protein encoded in pTE300.
Figure 19:
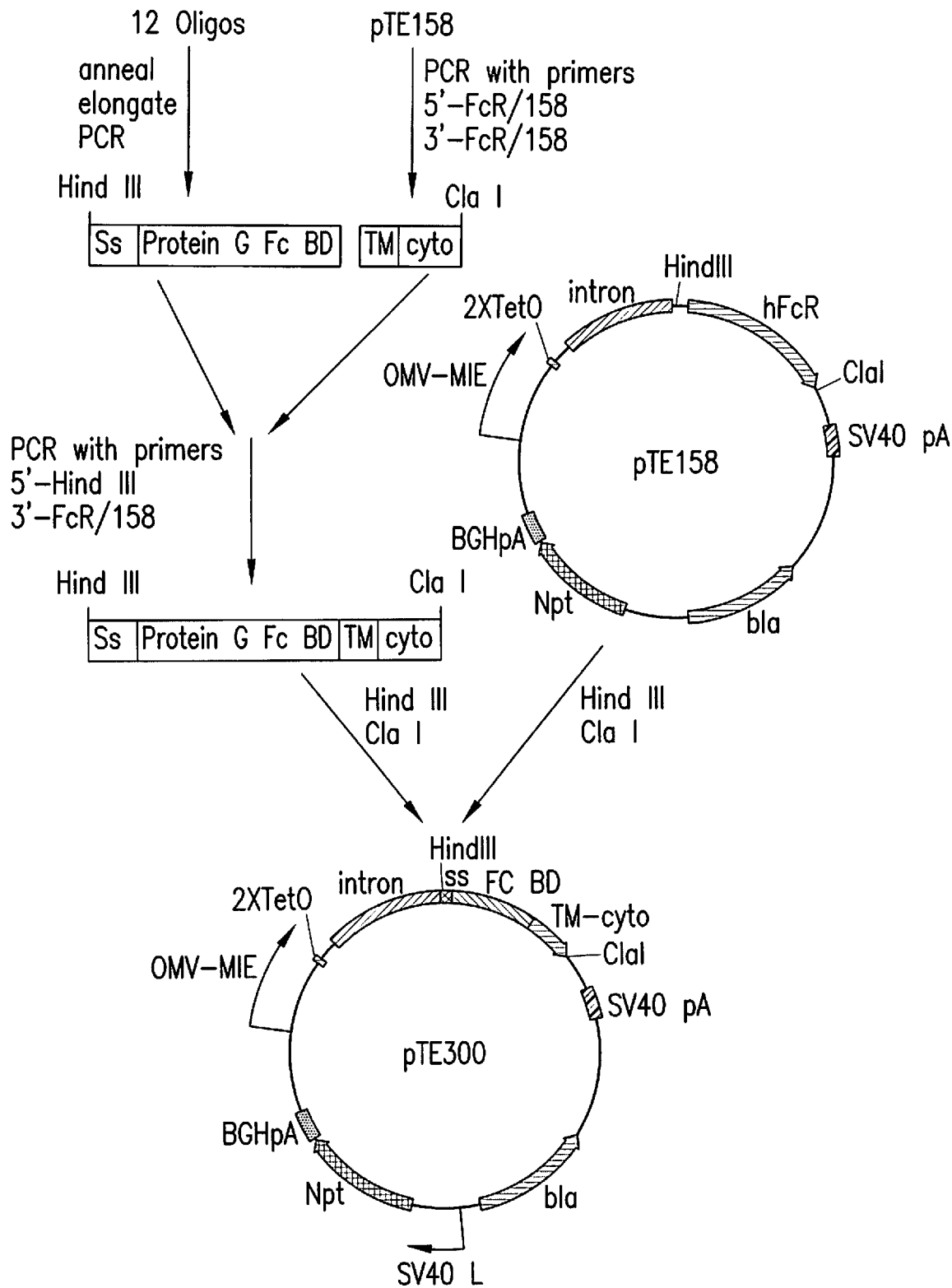
FIG. 19 is an outline of the construction of pTE300, designed for the expression of a chimeric protein containing the RORI signal sequence, the Fc binding domain of Protein G, and the transmembrane and intracellular domain of hFcγRI from the upstream CMV MIE promoter.
Figure 20A:
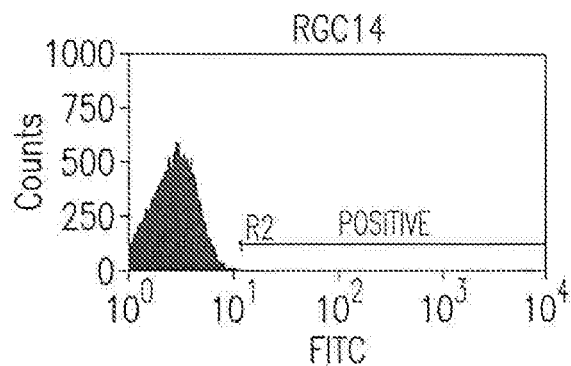
FIG. 20A shows a flow cytometry single parameter histogram of unstained RGC14 cells.
Figure 20B:
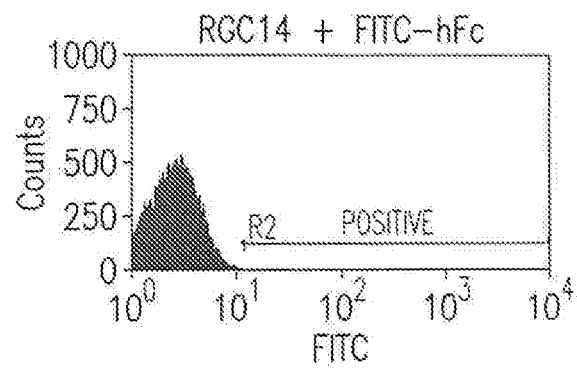
FIG. 20B shows a flow cytometry single parameter histogram of FITC-hFc stained RGC14 cells.
Figure 20C:
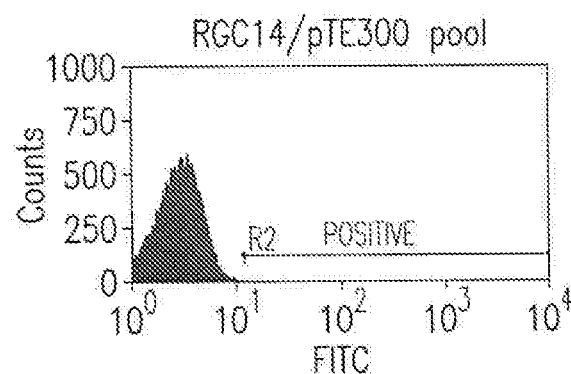
FIG. 20C shows a flow cytometry single parameter histogram of unstained G418-resistant RGC14 cell pool transfected with pTE300.
Figure 20D:
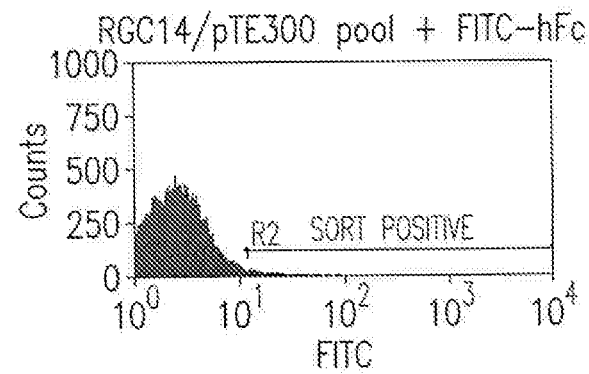
FIG. 20D shows a flow cytometry single parameter histogram of FITC-hFc stained G418-resistant RGC14 cell pool transfected with pTE300.
Figure 20E:
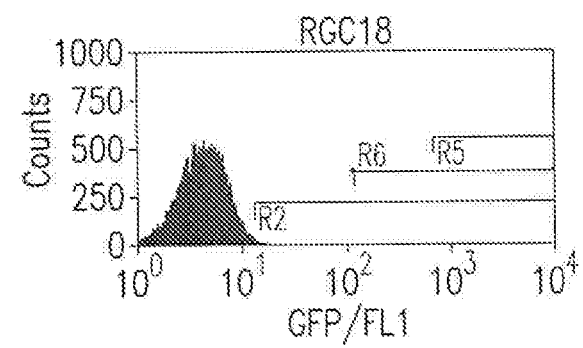
FIG. 20E shows a flow cytometry single parameter histogram of unstained RGC18 cells.
Figure 20F:
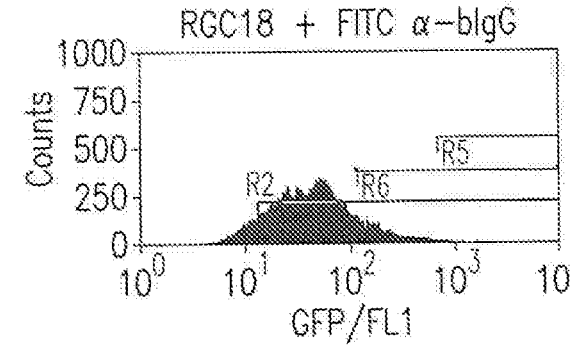
FIG. 20F shows a flow cytometry single parameter histogram of RGC18 cells incubated with 10% fetal bovine serum for 2 hours prior to staining with polyclonal FITC-conjugated anti-bovine IgG (H+L) F(ab')$_2$ fragment.

Example 8. Protein G Chimeric Protein can Function as a Cell Surface Capture Protein To demonstrate the application of the autologous secretion trap method to a cell surface capture protein other than hFcγRI, a cell line expressing Protein G was constructed. Protein G, from the *Streptococcus* strain G148, binds to all human and mouse IgG subclasses, and as such has utility for the isolation of recombinant cells expressing antibodies or IgG Fc fusion proteins. To demonstrate that the Protein G IgG Fc binding domain could be used as a cell surface capture protein capable of binding to all human and mouse IgG subclasses, we constructed a CHO line expressing a chimeric protein comprised of the Fc binding domain of Protein G fused to the hFcγRI transmembrane and intracellular domain (FIG. 18). The Fc binding domain of Protein G contains three homologous repeats of 55 amino acids long (Guss et al., (1986) EMBO 5:1567 and Sjobring et al., (1991) J. Biol. Chem. 266:399) and each repeat is capable of binding one IgG Fc. To improve the expression of this chimeric protein in CHO cells, we constructed a synthetic DNA in which the signal sequence from the mouse ROR1 gene was fused to the Fc binding domain, amino acids 303 to 497 of Protein G (accession # X06173) (SEQ ID NO:1). This synthetic DNA was generated by a combination of oligonucleotide annealing, gap filling, and PCR amplification. The synthetic DNA was then fused, by PCR, to DNA encoding the transmembrane and intracellular domains, amino acids 279 to 374 (SEQ ID NO:2), of hFcγRI (accession M21091). The resultant DNA encoding the Protein G/hFcγRI chimeric protein was cloned into pTE158 downstream of the CMV-MIE promoter, replacing the gene encoding hFcγRI, to yield the plasmid pTE300 (FIG. 19).

A CHO K1 cell line adapted to grow in serum-free medium, RGC14, was transfected with pTE300, and after three days 400 μg/ml G418 was added to the culture medium to select for stable integration of pTE300. Two weeks after the start of selection, the cells were stained with FITC-hFc to identify cells that expressed hFcγRI. These cells were analyzed by flow cytometry and cells expressing hFcγRI were collected as a pool (FIG. 20). The cells were expanded for 10 days and the population of cells expressing hFcγRI was again isolated by flow cytometry. The cells were again expanded, stained with FITC-hFc, and single cells expressing high levels of the Protein G/hFcγRI chimeric protein were isolated by flow cytometry. Single cells that stained positive for FITC-hFc binding were sorted into medium composed of 10% fetal bovine serum, 90% Ham's F12, and 400 μg/ml G418. After two weeks incubation, 48 clones were examined for binding to bovine IgG present in the culture medium by staining with FITC-conjugated anti-bovine IgG F(ab)$_2$ fragment (Jackson ImmunoResearch Laboratories, West Grove, Pa.). One clone, RGC18 that stained positive with this antibody was chosen for further characterization.

Figure 21A:
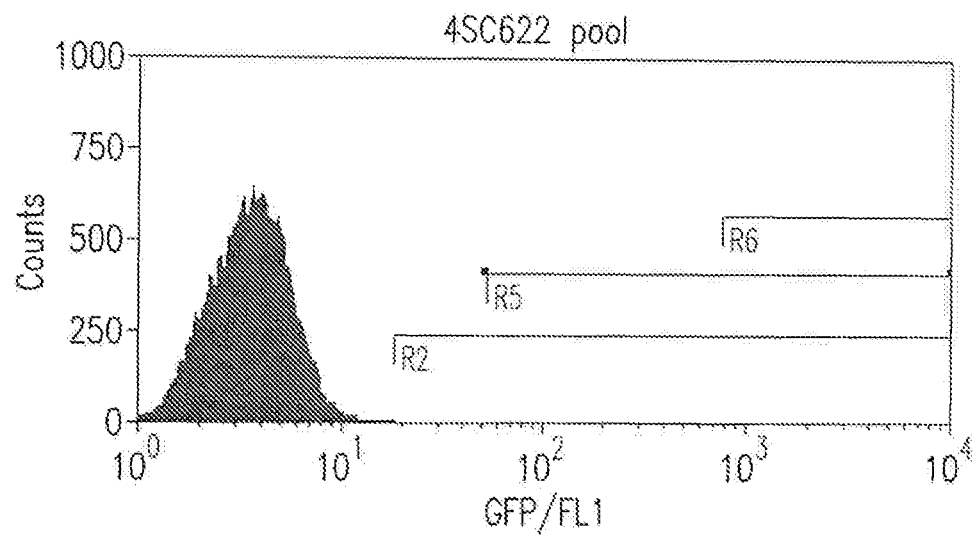
FIG. 21A shows a flow cytometry single parameter histogram of unstained hygromycin B-resistant cell pool derived from RGC18 after transfection with pTE209.
Figure 21B:
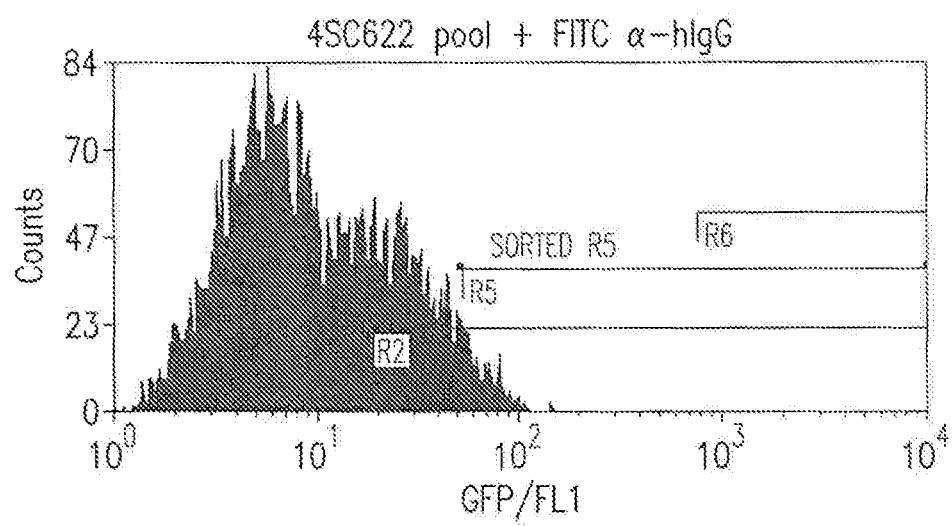
FIG. 21B shows a flow cytometry single parameter histogram of the hygromycin B-resistant cell pool derived from RGC18 after transfection with pTE209, incubated with rabbit IgG (1 mg/ml) for 18 hours prior to staining with polyclonal FITC-conjugated antihuman IgG (H+L) F(ab')$_2$ fragment.
Figure 22A:
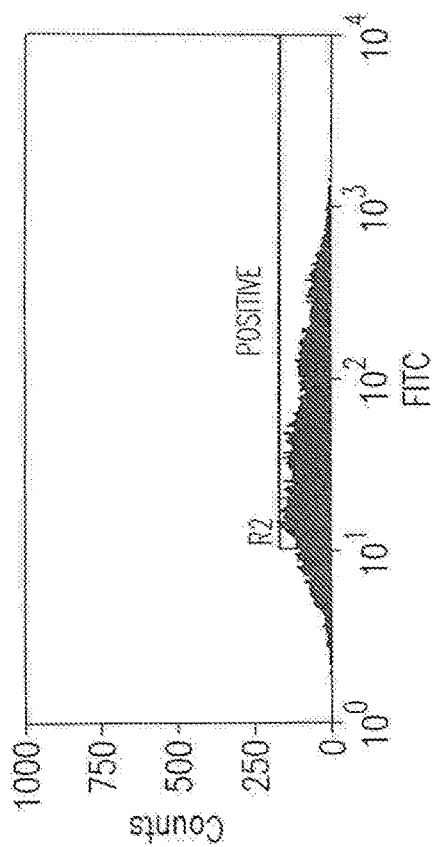
FIG. 22A shows a flow cytometry single parameter histogram of unstained RGC18 cells.
Figure 22B:
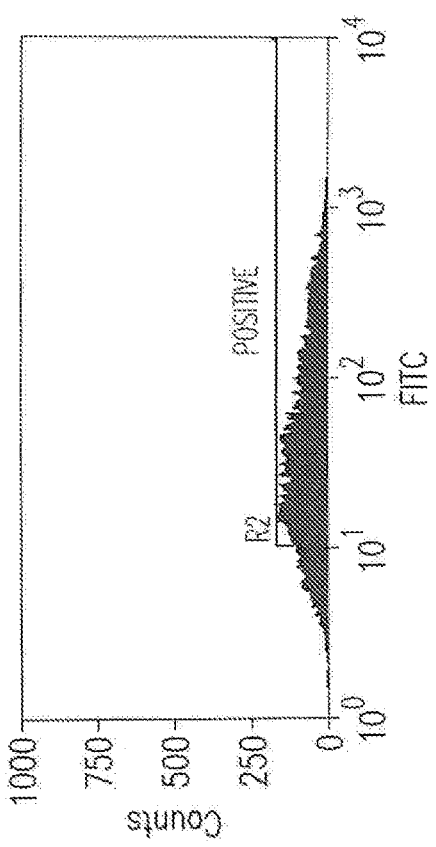
FIG. 22B shows a flow cytometry single parameter histogram of RGC18 cells incubated with 4SC622 (1 µg/ml) for 1 hour prior to staining with polyclonal FITC-conjugated anti-human IgG (H+L) F(ab')2 fragment.
Figure 22C:
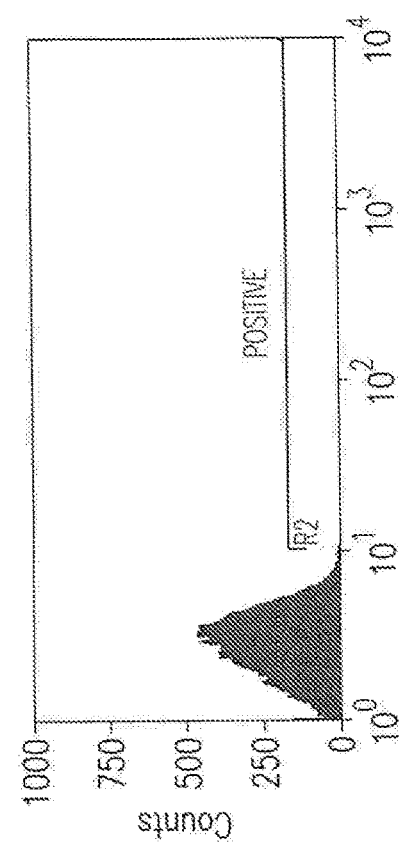
FIG. 22C shows a flow cytometry single parameter histogram of RGC18 cells incubated with 4SC622 (1 µg/ml) and rabbit IgG (1 mg/ml) for 1 hour prior to staining with polyclonal FITC-conjugated anti-human IgG (H+L) F(ab')$_2$ fragment.
Figure 22D:
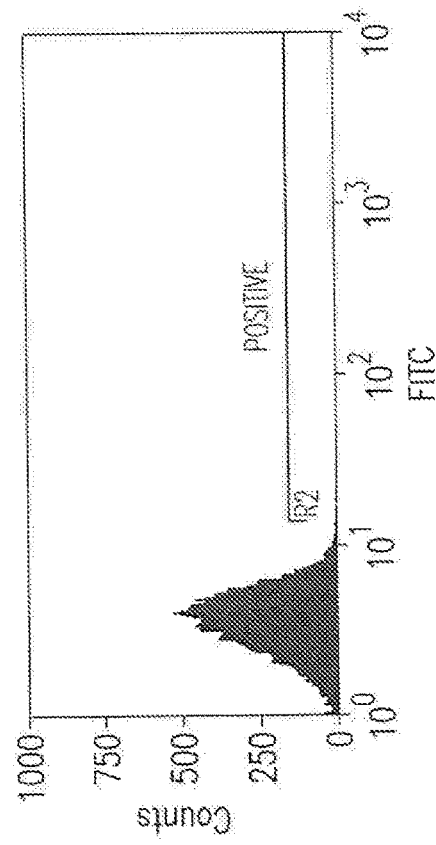
FIG. 22D shows a flow cytometry single parameter histogram of RGC18 cells incubated with 4SC622 (1 µg/ml) for 18 hours prior to staining with polyclonal FITC-conjugated anti-human IgG (H+L) F(ab')$_2$ fragment.
Figure 22E:
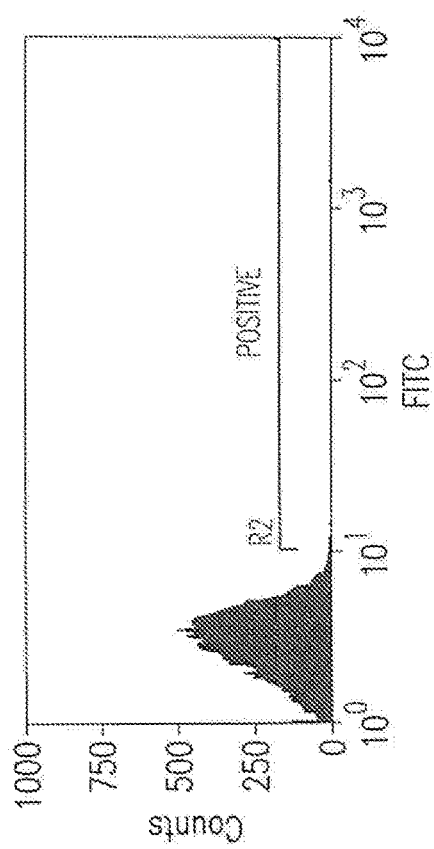
FIG. 22E shows a flow cytometry single parameter histogram of RGC18 cells incubated with 4SC622 (1 µg/ml) for 2 hours then with 4SC622 (1 µg/ml) and rabbit IgG (1 mg/ml) for 18 hours prior to staining with polyclonal FITC-conjugated anti-human IgG (H+L) F(ab')$_2$ fragment.
Figure 22F:
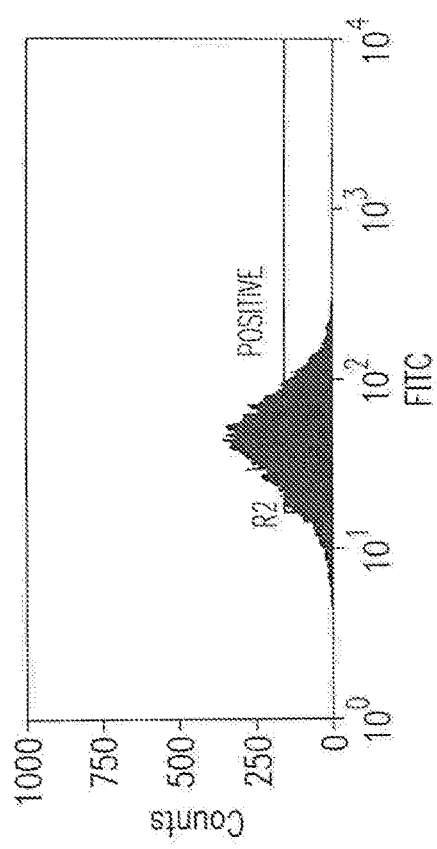
FIG. 22F shows a flow cytometry single parameter histogram of unstained RGC19 cells derived from RGC18 cells by transfection with pTE209.
Figure 22G:
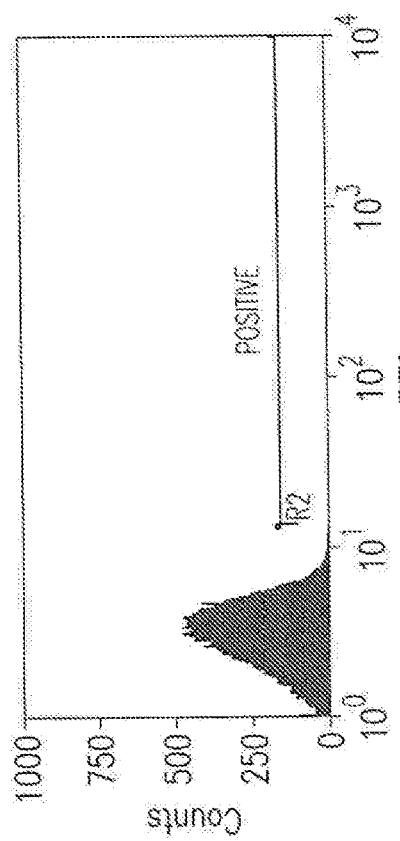
FIG. 22G shows a flow cytometry single parameter histogram of RGC19 cells stained with polyclonal FITC-conjugated anti-human IgG (H+L) F(ab')$_2$ fragment.
Figure 22H:
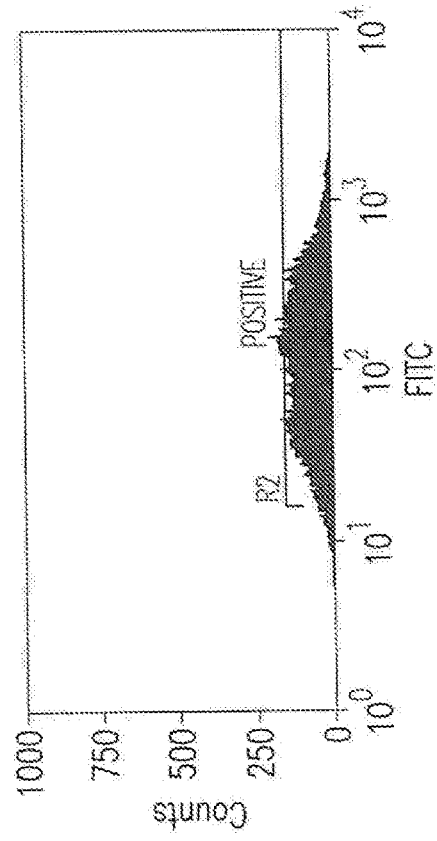
FIG. 22H shows a flow cytometry single parameter histogram of RGC19 cells incubated with rabbit IgG (1 mg/ml) for 18 hours prior to staining with polyclonal FITC-conjugated anti-human IgG (H+L) F(ab')$_2$ fragment.

Isolation of expression clones in RGC18: RGC18 cells (6×10$^6$) were transfected with pTE209 and selected for integration of the plasmid by growth in 400 μg/ml hygromycin for 18 days. Hygromycin-resistant cells were incubated with 1 mg/ml rabbit IgG for eighteen hours prior to staining with polyclonal FITC-conjugated anti-human IgG (H+L) F (ab')$_2$ fragment. Cells were stained for 1 hour then washed twice with PBS prior to analysis by flow cytometry (FIG. 21). The most fluorescent cells (top 5%) were isolated by single cell sorting and expanded for 3 weeks. Ten clones were examined for 4SC622 secretion. All clones tested secreted 4SC622 at high level, and the best clone, RGC19, had a specific productivity of 6.4 μg/cell day. This result demonstrated that 4SC622-expressing cells were efficiently isolated from a heterogeneous pool of cells derived from stable transfection of RGC18 with pTE209 by the autologous secretion trap method. Furthermore, these data clearly demonstrated that a fragment of Protein G could be engineered to include a signal sequence and transmembrane domain, and function as a cell surface capture protein.

To confirm that 4SC622 was autologously displayed on the surface of RGC19 cells expressing both Protein G/hFcγRI chimeric protein and 4SC622, RGC19 was incubated with 1 mg/ml rabbit IgG for 18 hours then stained with FITC-conjugated anti-human IgG (H+L) F(ab')$_2$ fragment and analyzed by flow cytometry. RGC19 cells were found to possess cell surface 4SC622 under these conditions in which cross-feeding was blocked by rabbit IgG, suggesting autologous display of 4SC622 (FIG. 22). Rabbit IgG effectively blocked binding of exogenous 4SC622 protein to RGC18 cells, but did not block display of 4SC622 on the cell surface of cells expressing 4SC622. These data demonstrated that the properties of the Protein G/hFcγRI chimeric protein were similar to those of hFcγRI as a cell surface capture protein, and suggested that the autologous secretion trap method can employ other proteins as cell surface capture proteins.

Example 9: Isolation of Antibody-Producing Cells from RGC10

To demonstrate the utility of the autologous secretion trap method for the isolation of CHO cell lines that express recombinant antibodies we cloned the DNA encoding variable light and variable heavy genes from the KD5 hybridoma. KD5 is a hybridoma that expresses a monoclonal antibody specific for the human Tie-2 receptor.

The mouse IgG constant region gene sequences were cloned from 500 ng of mouse spleen polyA+ RNA (Clontech, Palo Alto, Calif.). Single stranded cDNA was synthesized using SuperScript First-Strand Synthesis System for RT-PCR, primed with 50 ng of random hexamers (Invitrogen Life Technologies, Carlsbad, Calif.). The mouse kappa light constant DNA sequence (accession # Z37499) was amplified from this cDNA by PCR using the primers 5' mCLK1 (Z37499) (5'-CGGGCTGATG CTGCACCAAC TGTATCCATC TTC-3') (SEQ ID NO:3) and 3' mCLK1 (Z37499) (5'-ACACTCTCCC CTGTTGAAGC TCTT-GACAAT GGG-3') (SEQ ID NO:4). The mouse IgG2a constant region DNA sequence (accession # AJ294738) was also amplified from this cDNA by PCR using the primers 5' mCH2a (AJ294738) (5'-GCCAAAACAA CAGCCCCATC GGTCTATCCA C-3') (SEQ ID NO:5) and 3' mCH2a (AJ294738) (5'-TCATTTACCC GGAGTCCGGG AGAAGCTCTT AGTCG-3') (SEQ ID NO:6). The PCR products were cloned into pCR2.1-TOPO using TOPO TA Cloning kit (Invitrogen Life Technologies, Carlsbad, Calif.) and the sequence of the constant regions were verified.

The KD5 variable region genes were amplified by RT-PCR from KD5 hybridoma mRNA and cloned into pCR2.1-TOPO using the heavy and light chain variable region primer mixes from Amersham-Pharmacia Biotech (Piscataway, N.J.). The variable heavy chain gene was PCR amplified using the pCR2.1-TOPO cloned variable region as template with the primers 5' BspMI/KD5VH N— term (5'-GAGAGTACCT GCGTCATGCA GATGTGAAAC TGCAGGAGTC TGGCCCT-3') (SEQ ID NO:7) and 3' BspMI/KD5VH C— term (5'-GAGAGACCTG CGTCA-GCTGA GGAGACGGTG ACCGTGGT-3') (SEQ ID NO:8), digested with BspMI and ligated to the BsaI-digested IgG2a constant heavy gene PCR fragment amplified with the primers 5' BsaI/CH2a N— term (5'-GAGAGGGTCT CACAGCCAAA ACAACAGCCC CATCG-3') (SEQ ID NO:9) and 3' BsaI/CH2a C— term (5'-GAGAGGGTCT CCGGCCGCTC ATTTACCCGG AGTCCGGG AGAA-3') (SEQ ID NO:10). This fragment was then ligated into the BspMI and NotI sites of pRG882. The resulting plasmid, pTE317, was capable of expressing the KD5 recombinant heavy chain gene, fused to the mROR1 signal sequence, from the CMV-MIE promoter. The variable light chain gene was PCR amplified using the pCR2.1-TOPO cloned variable region as template with the primers 5' BsmBI/KD5VL N— term (5'-GAGAGCGTCT CATGCAGACA TCCAGAT- GAC CCAGTCTCCA-3') (SEQ ID NO:11) and 3' BsmBI/KD5VL C— term (5'-GAGAGCGTCT CACAGCCCGT TTTATTTCCA GCTTGGTCCC-3') (SEQ ID NO:12), digested with BsmBI and ligated to the BsaI-digested kappa constant light gene PCR fragment amplified with the primers 5' BsaI/CLK N— term (5'-GAGAGGGTCT CAGCT-GATGC TGCACCAACT GTATCC-3') (SEQ ID NO:13) and 3' BsaI/CLK C— term (5'-GAGAGGGTCT CAGGC-CGCTC AACACTCTCC CCTGTTGAAG CTCTTGAC-3') (SEQ ID NO:14). This fragment was then ligated into the BspMI and NotI sites of pRG882. The resulting plasmid, pTE316, was capable of expressing the KD5 recombinant light chain gene, fused to the mROR1 signal sequence, from the CMV-MIE promoter.

The 1450 bp EcoRI-NotI fragment from pTE317, encoding the KD5 heavy chain gene, was cloned into the EcoRI and NotI sites of pRG980, a vector that confers resistance to hygromycin and allows expression of recombinant genes for the UbC promoter, to yield plasmid pTE322. Similarly, the 750 bp EcoRI-NotI fragment from pTE316, encoding the KD5 light chain gene, was cloned into the EcoRI and NotI sites of pRG985, a vector that confers resistance to puromycin and allows expression of recombinant genes for the UbC promoter, to yield plasmid pTE324. RGC10 cells ($5\times10^6$) were transfected with 3 μg pTE322 and 3 μg pTE322 and selected for integration of the plasmids by growth in F12 medium supplemented with 10% fetal calf serum with 20 μg puromycin and 400 μml hygromycin for 14 days. Expression of hFcγRI was induced by the addition of 1 μg/ml of doxycycline to the culture medium for three days. Double-resistant cells were incubated with 1 mg/ml rabbit IgG for eighteen hours prior to staining with goat polyclonal FITC-conjugated anti-mouse IgG (Fcγ) F $(ab')_2$ fragment (Jackson ImmunoResearch Laboratories, West Grove, Pa.). Cells were stained for 1 hour then washed twice with PBS prior to analysis by flow cytometry. The most fluorescent cells (top 5%) were isolated as a pool and expanded for 10 days, after which the protocol was repeated but the top 1% most fluorescent cells were isolated as a pool. This pool was expanded for 10 days then the top 0.1% most fluorescent cells were isolated as single cells into 96-well plates. Clones were analyzed by ELISA for expression of antibody and seven clones were chosen from 53 clones analyzed. The average specific productivity of these clones was 35 μg/cell/day and the best clone expressed the recombinant KD5 monoclonal antibody at 54 μg/cell/day.

Example 10: FASTR Screens Unaffected by CSCP Expression Level

To demonstrate that the expression level of the CSCP does not significantly affect the ability to isolate cells expressing an associated sPOI, FASTR screens for the same sPOI in two different host cell lines that each express the same CSCP but at either a high level or a low level were compared.

The FASTR host cell line RGC10 was selected for high-level expression of hFcγRI protein by stable integration of pTE158 and was found to contain 40 hFcγRI integrated gene copies. A new cell line, RS527, that expressed hFcγRI protein at a lower level, was generated from CHO K1 after stable transfection and selection for single copy gene integration. RS527 cells expressed significantly less hFcγRI protein than RGC10 cells as determined by Western blot analysis of whole cell lysates of the FASTR cell lines.

Briefly, RGC10 and RS527 cells were transfected with pTE462, a plasmid capable of expressing a secreted hFc-fusion protein Rc1-hFc and conferring resistance to hygromycin. The transfected cultures were selected with hygromycin for two weeks. The hygromycin-resistant cells were induced with 1 μg/ml doxycycline (Dox) and blocked with rabbit IgG overnight, following the FASTR method described herein. The next day, the RGC10/pTE462 and RS527/pTE462 cultures were stained by a FITC-conjugated antibody specific for hFc and then analyzed by flow cytometry. Three cell bins R4, R5, and R6 marking cells with low, medium, and high fluorescence respectively were sorted from each host line and expanded in tissue culture.

To compare Rc1-hFc protein production level from the six cell bins, six cultures were set up using equal number of cells for each bin. Three days later, conditioned media were collected. The Rc1-hFc protein titers in the conditioned media were determined by ELISA and were plotted against mean fluorescence of the respective cell bins. For both RGC10 and RS527 host lines, there was a similar correlation between mean fluorescence (amount of Rc1-hFc displayed on the cell surface) and sPOI protein production levels of the isolated cell pools. Most significantly, the sPOI titers in the two high fluorescence R6 bins derived from RGC10 and RS527 were similar. These data demonstrate that the expression level of the CSCP in a FASTR host cell line does not significantly affect the use of that host to isolate transfected cells based on expression level of a sPOI.

Example 11: Tie2 Receptor as a Cell Surface Capture Protein

Cell surface capture proteins (CSCP's) other than FcγRI can be used in the methods described herein. In this example, the Tie2 receptor functions as a CSCP and is used to isolate cells expressing a Tie-specific $ScFv_{C1b}$-Fc fusion protein made from the C1b monoclonal antibody that specifically binds the extracellular domain of Tie2 receptor. Although the CSCP for $ScFv_{C1b}$-Fc can be hFcγRI, this example demonstrates that Tie2 can also be used as the CSCP for $ScFv_{C1b}$-Fc.

To construct an inducible Tie2 CSCP cell line, CHO K1 was first stably transfected with the TetR plasmid pcDNA6/TR. The blasticidin-resistant cell pool was then stably transfected with pTE259, a plasmid that allows inducible expression of a protein comprised of the extracellular domain and transmembrane domain of Tie2. Inducible cell clones were isolated by flow cytometry after staining with an antibody specific for Tie2 (FIG. 3). The RGC54 clone was chosen to study the feasibility of FASTR for the expression of $ScFv_{C1b}$-Fc.

RGC54 cells were stably transfected with pTE988, a plasmid capable of expressing the secreted hFc-fusion protein $ScFv_{C1b}$-Fc and conferring resistance to hygromycin. The transfected culture was selected with hygromycin for two weeks. The hygromycin-resistant cells were induced with Dox and blocked with 1 mg/ml of purified C1b mAb. The C1b monoclonal antibody was the source of the variable regions in $ScFv_{C1b}$-Fc. The next day, the cell pool was stained by a FITC-conjugated antibody specific for hFc and then analyzed by flow cytometry. Three cell bins R6, R7, and R8 marking cells with high, medium, and low fluorescence respectively were sorted and expanded in tissue culture. Three cultures were set up using an equal number of cells for each bin to determine $ScFv_{C1b}$-Fc protein production as determined by ELISA. A correlation existed between mean fluorescence (amount of $ScFv_{C1b}$-Fc binding to Tie2 on the cell surface) and $ScFv_{C1b}$-Fc protein production levels of the isolated cell pools.

These data show that CSCP other than hFcγRI can serve as a CSCP, and also suggest that any receptor may be converted into a CSCP by removal of its cytoplasmic domain. These data also demonstrate that an antigen can be made into a CSCP and used for FASTR screening cells expressing an antigen-specific antibody-related molecule.

Example 12: Effective FASTR Screens with CSCP:sPOI Pairs Having Low Affinity

Angiopoetin-1 is a ligand for the Tie2 receptor. A chimeric protein comprising angiopoetin-1 receptor binding domain and hFc (FD1-hFc) binds to Tie2 with an affinity constant of 174 nM as determined by BIAcore™. FD1-hFc and Tie2 were chosen as sPOI and CSCP, respectively, to determine if a minimum affinity between CSCP and sPOI is required for FASTR screens In cell decoration experiments, exogenously added FD1-hFc bound specifically to RGC54 cells through Tie2. To determine if the affinity between Tie2 and FD1-hFc is sufficient to allow FASTR screening, RGC54 cells were stably transfected with pTE942, a plasmid capable of expressing the secreted hFc-fusion protein FD1-hFc and conferring resistance to hygromycin. The transfected culture was selected with hygromycin for two weeks. The hygromycin-resistant cells were induced with Dox and blocked with 1 mg/ml of purified FD1-mFc comprising mouse IgG1 Fc. The next day, the cell pool was stained by a FITC-conjugated antibody specific for hFc and then analyzed by flow cytometry. Three cell bins R6, R7, and R8 marking cells with high, medium, and low fluorescence, respectively, were collected. Cultures were set up using equal number of cells for each bin to determine FD1-hFc protein production levels in the conditioned media as determined by ELISA. There was a correlation between mean fluorescence (FD1-Fc binding to cell surface-bound Tie2) and FD1-hFc protein production levels of the isolated cell pools. The bin with the highest fluorescence produced the most FD1-hFc.

These data demonstrate that a CSCP:sPOI pair with low affinity (174 nM KD) can be used for effective FASTR screens. Importantly, the dissociation $t_{1/2}$ for FD1-Fc: Tie2 binding is less than 2 minutes, suggesting that any CSCP:sPOI pair with a measurable affinity can work in FASTR screens. In addition, this experiment also shows that a non-FcγRI receptor may be used as the CSCP to isolate cells expressing its ligand.

Example 12: Fusing a Transmembrane Domain onto an ScFv Makes a Functional CSCP

An CSCP can be any cell surface-bound protein that has a measurable affinity to the sPOI. To demonstrate this, a totally synthetic CSCP was constructed by fusing the transmembrane domain from the PDGF receptor to an ScFv containing the variable regions from the murine kappa chain-specific monoclonal antibody HB58. A FASTR host was constructed that expresses this chimeric protein ($SCFV_{HB58}$-$TM_{PDGFR}$) and was used to isolate cells expressing the angiopoeitin-2 FD domain-specific P12 antibody.

The RS655 cell line, derived from CHO K1, constitutively expresses $ScFv_{HB58}$-$TM_{PDGFR}$. Cells expressing $ScFv_{HB58}$-$TM_{PDGFR}$ can be stained by sequential incubation with P12 mAb, FD2-hFc, and FITC-conjugated anti-hIgG—P12 detected on the cell surface by the HB58 ScFv was detected by its affinity for FD2, which in turn was detected by recognition of the hFc tag. RS656 cells were derived from RS655 cells after stable transfection with a plasmid encoding the gene for eYFP. Nearly 100% of RS656 cells were eYFP-positive, and most (76%) maintained expression of $ScFv_{HB58}$-$TM_{PDGFR}$ as detected by binding to FD2-hFc.

RS655 cells were stably transfected with pTE693, a plasmid capable of expressing the heavy and light chains of the P12 antibody, and conferring resistance to puromycin. The transfected culture was selected with puromycin for two weeks to yield a pool of cells that were heterogeneous with regard to P12 mAb expression (RS655/pTE693).

To determine if $ScFv_{HB58}$-$TM_{PDGFR}$ could function as a CSCP and facilitate isolation of antibody-producing cells from non-producers, equal numbers of RS656 cells and RS655/pTE693 cells were mixed and co-cultured. When P12 expressed from RS655/pTE693 cells was allowed to diffuse and bind to $ScFv_{HB58}$ on the surface of RS656 cells a large population of yellow cells were also positive for binding FD2-hFc. However, if the $ScFv_{HB58}$ on the surface of RS656 was bound with excess murine IgG, then only non-yellow cells were positive for binding FD2-hFc, demonstrating that expressing cells were effectively separated from non-expressing cells.

These data demonstrate that an ScFv can be made into a functional CSCP by targeting it to the cell membrane. The data also show that FASTR allows cells expressing a secreted antibody to be detected with the antibody's antigen.

Example 13: A Protein of Interest Comprising a T Cell Receptor Variable Region

A flow cytometry-based autologous secretion trap (FASTR) method for isolating high expression clones of a cell line that expresses a protein of interest that is a TCR-Fc is prepared in a manner analogous to preparing a cell line that expresses an antibody of interest. High expression clones are identified by screening cells that display on their surface the TCR-Fc of interest bound to hFcγR.

In these examples, the CHO K1 cell line RGC10, comprising an inducible FcγR1 as a cell surface capture molecule, is employed. RGC10 is made to express recombinant TCR-Fc's by cloning TCR variable regions, in frame, to a human Fc region either directly in frame or with a linker sequence between the TCR variable regions and the human Fc region.

To make a protein of interest that is a dimer comprising an Fc-linked TCR α variable domain and an Fc-linked TCR β variable domain, RGC10 is transfected with two vectors: a first vector capable of expressing a TCR α variable domain fusion protein with a human Fc sequence, and a second vector capable of expressing a TCR β domain fusion protein with the same human Fc sequence. Each vector includes leader sequence (e.g., a secretion signal sequence) 5' with respect to the TCR variable region. and a selectable marker that is a drug resistance gene. Following each vector transfection, cells containing the vector are selected by an appropriate drug selection. The selection results in an RGC10 cell line having both the first and the second vectors. Cells expressing proteins of interest can be detected by one or more of an antibody to the β variable domain, an antibody to the α variable domain, and an antibody to the Fc domain.

To make a protein of interest that is a dimer comprising both an α and a β TCR variable domain fused to an Fc, RGC10 is transfected with a single vector encoding a protein of interest that is constructed as follows: a leader sequence (e.g., a secretion signal sequence), followed by a TCR variable β domain fused to a linker, where the linker is, in turn, fused to a TCR variable α domain, which in turn is fused to an Fc sequence. Alternatively, the single vector can be constructed as follows: a leader sequence (e.g., a secretion signal sequence), followed by a TCR variable α domain fused to a linker, where the linker is, in turn, fused to a TCR variable β domain, which in turn is fused to an Fc sequence. Cells expressing proteins of interest can be detected by one or more of an antibody to the β variable domain, an antibody to the α variable domain, and an antibody to the Fc domain.

To make proteins of interest, as above, which also comprise a TCR α and/or TCR β constant domain, the TCR variable domain (α or β) is fused to a TCR constant domain (e.g., TCR variable domain α is fused to TCR constant domain α, and TCR variable domain β is fused to TCR constant domain β), and the TCR variable+constant domain is fused directly or through a linker to the Fc domain. Cells expressing proteins of interest can be detected by one or more of an antibody to the β variable domain, an antibody to the α variable domain, and an antibody to the Fc domain.

Cells expressing desired amounts of the TCR-Fc are isolated using the same procedure as used in isolating 4SC622-producing cell lines described herein, using one or more of an antibody to the α variable domain, an antibody to the β variable domain, an antibody to the α constant domain, and antibody to the β constant domain, and an antibody to the Fc domain. Cells expressing the highest levels of the TCR-Fc are selected as TCR-Fc-producing cell lines.

Although the foregoing invention has been described in some detail by way of illustration and example, it will be readily apparent to those of ordinary skill in the art that certain changes and modifications may be made to the teachings of the invention without departing from the spirit or scope of the appended claims.

What is claimed:

1. A method of high expression of a protein of interest, comprising:
   (a) transfecting a mammalian cell with (i) a nucleic acid encoding the protein of interest and (ii) a nucleic acid encoding a cell surface capture molecule that comprises a membrane anchor and is capable of binding the protein of interest;
   (b) culturing the mammalian cell under conditions in which the protein of interest and cell surface capture molecule are expressed, and a protein of interest-cell surface capture molecule complex is formed and displayed on the cell surface of the mammalian cell;
   (c) contacting the mammalian cell with a detection molecule that binds to the protein of interest-cell surface capture molecule complex; and
   (d) detecting and isolating the mammalian cell that displays on the cell surface the binding of the detection molecule with the protein of interest-cell surface capture molecule complex.

2. The method of claim 1, wherein the method further comprises (e) culturing the isolated mammalian cell under conditions in which the protein of interest is expressed and secreted from the cell.

3. The method of claim 1, wherein the protein of interest is selected from the group consisting of an antibody, a Fab, a single chain antibody (ScFv), anything fused to an antibody constant region, ligand, a soluble receptor protein, a growth factor, or a fragment thereof.

4. The method of claim 1, wherein the cell surface capture molecule is selected from the group consisting of a ligand-specific receptor, a receptor-specific ligand, an antibody-binding protein, an antibody, a single chain antibody (ScFv), a peptide, or a fragment thereof.

5. The method of claim 4, wherein the antibody binding protein is an Fc receptor, anti-immunoglobulin antibodies, anti-immunoglobulin ScFv, Protein A, Protein L, Protein G, Protein H or functional fragments thereof.

6. The method of claim 1, wherein the membrane anchor is a transmembrane anchor.

7. The method of claim 6, wherein the transmembrane anchor remains anchored in the cell membrane and exposed to the outside of the cell.

8. The method of claim 1, wherein the membrane anchor may be native to the cell, recombinantly expressed in the cell, or synthetic to the cell.

9. The method of claim 1, wherein the cell surface capture molecule specifically binds an antibody as the protein of interest.

10. The method of claim 9, wherein the antibody is selected from the group consisting of IgM, IgG, IgA, IgD or IgE, or various subtypes thereof.

11. The method of claim 1 further comprising the step after (c) of contacting the cell with a blocking molecule which binds the cell surface capture molecule to reduce diffusion of the protein of interest between cells.

12. The method of claim 1, wherein the detection molecule comprises two molecules that bind each other and are differentially labeled.

13. The method of claim 1, wherein the detection molecule is linked to a solid support or particle.

14. The method of claim 1, wherein the nucleic acid encoding the cell surface capture molecule is stably integrated in the cell.

15. The method of claim 1, wherein the nucleic acid encoding the protein of interest and the nucleic acid encoding the cell surface capture molecule are introduced into the cell simultaneously.

16. The method of claim 15, wherein the nucleic acid encoding the protein of interest and the nucleic acid encoding the cell surface capture molecule are introduced into the cell on the same vector or plasmid.

17. The method of claim 1, wherein the cell is detected and isolated in step (d) by flow cytometry.

18. The method of claim 1, further comprising repeating steps (b)-(d) to enrich and detect high expression cells of the protein of interest.

19. A method of isolating a mammalian cell with high expression of a secreted protein of interest (POI), comprising:
   (a) transfecting a mammalian cell with a nucleic acid that encodes a secreted POI and a cell surface capture molecule capable of binding the POI, wherein the secreted POI and the cell surface capture molecule are both expressed by the cell, wherein the cell surface capture molecule comprises a protein, or a functional fragment thereof which comprises a membrane anchor;
   (b) culturing the cell under conditions in which the POI and cell surface capture molecule are expressed, and a POI-cell surface capture molecule complex is formed and displayed on the cell surface;
   (c) contacting the cell with a detection molecule, which binds to the POI displayed by the cell; and
   (d) detecting and/or isolating the cell due to it being bound to the detection molecule.

20. The method of claim 1, wherein the cell surface capture molecule comprises an antibody, an antibody fragment, a protein, or a functional fragment thereof which comprises the membrane anchor.

* * * * *